(12) United States Patent
Arinzeh et al.

(10) Patent No.: US 10,772,909 B2
(45) Date of Patent: Sep. 15, 2020

(54) SYSTEM AND METHOD FOR INSULIN-MIMETIC OF CARTILAGE, BONE, OR OSTEOCHONDRAL REPAIR AND PIEZOELECTRIC COMPOSITE SCAFFOLD

(71) Applicant: New Jersey Institute of Technology, Newark, NJ (US)

(72) Inventors: Treena Lynne Arinzeh, West Orange, NJ (US); Ateka Khader, Kearny, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 307 days.

(21) Appl. No.: 15/722,299

(22) Filed: Oct. 2, 2017

(65) Prior Publication Data

US 2018/0092943 A1 Apr. 5, 2018

Related U.S. Application Data

(60) Provisional application No. 62/401,979, filed on Sep. 30, 2016, provisional application No. 62/402,064, filed on Sep. 30, 2016.

(51) Int. Cl.
| | |
|---|---|
| *A61K 33/24* | (2019.01) |
| *A61K 35/28* | (2015.01) |
| *A61K 47/02* | (2006.01) |
| *A61K 47/34* | (2017.01) |
| *A61L 27/54* | (2006.01) |
| *A61K 33/30* | (2006.01) |
| *A61L 27/38* | (2006.01) |
| *A61L 27/44* | (2006.01) |
| *A61L 27/18* | (2006.01) |
| *A61L 27/50* | (2006.01) |

(52) U.S. Cl.
CPC ............. *A61K 33/24* (2013.01); *A61K 33/30* (2013.01); *A61K 35/28* (2013.01); *A61K 47/02* (2013.01); *A61K 47/34* (2013.01); *A61L 27/18* (2013.01); *A61L 27/3834* (2013.01); *A61L 27/446* (2013.01); *A61L 27/50* (2013.01); *A61L 27/54* (2013.01); *A61L 2300/102* (2013.01); *A61L 2300/412* (2013.01); *A61L 2400/12* (2013.01)

(58) Field of Classification Search
CPC ........ A61K 33/24; A61K 33/30; A61K 47/34; A61K 47/02; A61K 35/28; A61L 27/50; A61L 27/18; A61L 27/446; A61L 27/3834; A61L 27/54; A61L 2400/12; A61L 2300/412; A61L 2300/102
See application file for complete search history.

(56) References Cited

U.S. PATENT DOCUMENTS

2013/0052254 A1* 2/2013 Arinzeh .................. A61L 27/16
424/443
2015/0010499 A1* 1/2015 Lin ......................... A61K 33/24
424/85.2

FOREIGN PATENT DOCUMENTS

WO WO-2012069560 A2 * 5/2012 .............. C08L 89/06

OTHER PUBLICATIONS

Chhabra, Hemlata et al., "A Nano Zinc Oxide Doped Electrospun Scaffold Improves Wound Healing in a Rodent Model", Dec. 24, 2015, Royal Society of Chemistry (RSC) Advances, vol. 6, No. 2, 2016, pp. 1428-1439.*
Ullah et al., Human mesenchymal stem cells—current trends and future prospective, Biosci Rep, Apr. 2015, vol. 35 (2), p. e00191.
Vega et al., Treatment of Knee Osteoarthritis With Allogeneic Bone Marrow Mesenchymal Stem Cells: A Randomized Controlled Trial, Transplantation, Aug. 2015, vol. 99(8), pp. 1681-1690.
Zafra et al., Sodium tungstate activates glycogen synthesis through a non-canonical mechanism involving G-proteins, FEBS Letters, Jan. 2013, vol. 587, Issue 3, pp. 291-296.
Abrams et al., BioCartilage: Background and Operative Technique, Operative Techniques in Sports Medicine, Jun. 2013, vol. 21, Issue 2, pp. 116-124.
Arita et al., Activation of the extracellular signal-regulated kinases 1 and 2 (ERK1/2) is needed for the TGF?-induced chondrogenic and osteogenic differentiation of mesenchymal stem cells, Biochemical and Biophysical Research Communications, Feb. 2011, vol. 405, Issue 4, pp. 564-569.
Barbera et al., Effects of tungstate in neonatally streptozotocin-induced diabetic rats: mechanism leading to normalization of glycaemia, Diabetologia, Jan. 1997, vol. 40, Issue 2, pp. 143-149.
Barbera et al., Insulin-like actions of tungstate in diabetic rats. Normalization of hepatic glucose metabolism., The Journal of Biological Chemistry, Aug. 1994, vol. 269, pp. 20047-20053.

(Continued)

*Primary Examiner* — Louise W Humphrey
*Assistant Examiner* — Anjali Ajit Hirani
(74) *Attorney, Agent, or Firm* — Lerner, David, Littenberg, Krumholz & Mentlik, LLP

(57) ABSTRACT

Shown and described is an insulin-mimetic as an inductive agent for cartilage and/or bone repair is disclosed. Sodium tungstate ($Na_2WO_4$) was utilized as an inductive factor to enhance human mesenchymal stem cell (MSC) chondrogenesis. The chondrogenic differentiation of MSCs was enhanced in the presence of low concentrations of $Na_2WO_4$ as compared to control, without $Na_2WO_4$. Also disclosed is a composite scaffold capable of supporting cell and tissue growth. The composite scaffold could include zinc oxide and polycaprolactone.

10 Claims, 10 Drawing Sheets

(4 of 10 Drawing Sheet(s) Filed in Color)

(56) References Cited

OTHER PUBLICATIONS

Beam et al., The effects of blood glucose control upon fracture healing in the BB Wistar rat with diabetes mellitus, Journal of Orthopaedic Research, Nov. 2002, vol. 20, Issue 6, pp. 1210-1216.
Bertinat et al., Preclinical and Clinical Studies for Sodium Tungstate: Application in Humans, J Clin Cell Immunol, Feb. 2015, vol. 6, No. 1, p. 285.
Brange et al., Insulin structure and stability, Pharm Biotechnol, Jan. 1993, vol. 5, pp. 315-350.
Chang et al., Involvement of Gas7 along the ERK1/2 MAP kinase and SOX9 pathway in chondrogenesis of human marrow-derived mesenchymal stem cells, Osteoarthritis Cartilage, Nov. 2008, vol. 16, Issue 11, pp. 1403-1412.
Dedania et al., Role of local insulin augmentation upon allograft incorporation in a rat femoral defect model, Journal of Orthopaedic Research, Jan. 2011, vol. 29, Issue 1, pp. 92-99.
Desai et al., Pollen-induced antigen presentation by mesenchymal stem cells and T cells from allergic rhinitis, Clin Transl Immunology, Oct. 2013, vol. 2, p. e7.
Dhollander et al., Midterm results of the treatment of cartilage defects in the knee using alginate beads containing human mature allogenic chondrocytes, Am J Sports Med, Jan. 2012, vol. 40(1), pp. 75-82.
Diekman et al., Chondrogenesis of adult stem cells from adipose tissue and bone marrow: induction by growth factors and cartilage-derived matrix, Tissue Eng Part A, Feb. 2010, vol. 16, Issue 2, pp. 523-533.
Dominguez et al., The antidiabetic agent sodium tungstate activates glycogen synthesis through an insulin receptor-independent pathway, J Biol Chem, Oct. 2003, vol. 278(44), pp. 42785-42794.
Dominici et al, Minimal criteria for defining multipotent mesenchymal stromal cells. The International Society for Cellular Therapy position statement, Cytotherapy, Jan. 2006, vol. 8, Issue 4, pp. 315-317.
Gandhi et al., The effects of local insulin delivery on diabetic fracture healing, Bone, Oct. 2005, vol. 37, Issue 4, pp. 482-490.
Gomez-Ramos et al., Inhibition of GSK3 dependent tau phosphorylation by metals, Curr Alzheimer Res, Apr. 2006, vol. 3(2), pp. 123-127.
Gomez-Ramos et al., Sodium tungstate decreases the phosphorylation of tau through GSK3 inactivation, J Neurosci Res, Feb. 2006, vol. 83, Issue 2, pp. 264-273.
Greco et al., AMD3100-mediated production of interleukin-1 from mesenchymal stern cells is key to chemosensitivity of breast cancer cells, Am J Cancer Res, Jun. 2011, vol. 1(6), pp. 701-715.
Guandalini et al., Tissue distribution of tungsten in mice following oral exposure to sodium tungstate, Chem Res Toxicol, Apr. 2011, vol. 24(4), pp. 488-493.
Hanzu et al., Proof-of-concept trial on the efficacy of sodium tungstate in human obesity, Diabetes Obes Metab, Nov. 2010, vol. 12, Issue 11, pp. 1013-1018.
Haynesworth et al., Cell surface antigens on human marrow-derived mesenchymal cells are detected by monoclonal antibodies, Bone, Jan. 1992, vol. 13, Issue1, pp. 69-80.
Hreha et al., Local manganese chloride treatment accelerates fracture healing in a rat model, Journal of Orthopaedic Research, Jan. 2015, vol. 33, Issue 1, pp. 122-130.
Jaiswal et al., Osteogenic differentiation of purified culture-expanded human mesenchymal stem cells in vitro, Journal of Cellular Biochemistry, Feb. 1997, vol. 64, Issue 2, pp. 295-312.
Kapoor et al., Tolerance-like mediated suppression by mesenchymal stem cells in patients with dust mite allergy-induced asthma, J Allergy Clin Immunol, Apr. 2012, vol. 129, Issue 4, pp. 1094-1101.
Kellner et al., Insulin in tissue engineering of cartilage: a potential model system for growth factor application, J Drug Target, Feb. 2001, vol. 9, Issue 6, pp. 439-448.
Kelly et al., In vivo tungsten exposure alters B-cell development and increases DNA damage in murine bone marrow, Toxicological Sciences, Feb. 2013, vol. 131, Issue 2, pp. 434-446.
Lee et al., Long-term clinical study and multiscale analysis of in vivo biodegradation mechanism of Mg alloy, Proc Natl Acad Sci U S A, Jan. 2013, vol. 113, No. 3, pp. 716-721.
Li et al., Novel Magnesium Alloys Developed for Biomedical Application: A Review, Journal of Materials Science & Technology, Jun. 2013, vol. 29, Issue 6, pp. 489-502.
Lin et al., The chondrocyte: biology and clinical application, Tissue Eng, Jul. 2006, vol. 12, Issue 7, pp. 1971-1984.
Longobardi et al., Effect of IGF-I in the chondrogenesis of bone marrow mesenchymal stem cells in the presence or absence of TGF-beta signaling, J Bone Miner Res, Apr. 2006, vol. 21, Issue 4, pp. 626-636.
Madeira et al., Advanced cell therapies for articular cartilage regeneration, Trends Biotechnol, Jan. 2015, vol. 33, Issue 1, pp. 35-42.
Makris et al., Repair and tissue engineering techniques for articular cartilage, Nat Rev Rheumatol, Jan. 2015, vol. 11, Issue 1, pp. 21-34.
Mourino et al., Metallic ions as therapeutic agents in tissue engineering scaffolds: an overview of their biological applications and strategies for new developments, J R Soc Interface, Mar. 2012, vol. 9(68), pp. 401-419.
Mueller et al., Insulin is essential for in vitro chondrogenesis of mesenchymal progenitor cells and influences chondrogenesis in a dose-dependent manner, Int Orthop, Jan. 2013, vol. 37, Issue 1, pp. 153-158.
Munoz et al., Effects of tungstate, a new potential oral antidiabetic agent, in Zucker diabetic fatty rats, Diabetes, Jan. 2001, vol. 50(1), pp. 131-138.
Murphy et al., The impact of osteoarthritis in the United States: a population-health perspective: A population-based review of the fourth most common cause of hospitalization in U.S. adults, Orthop Nurs, Mar. 2012, vol. 31(2), pp. 85-91.
Nagareddy et al., Oral administration of sodium tungstate improves cardiac performance in streptozotocin-induced diabetic rats, Can J Physiol Pharmacol, May 2005, vol. 83(5), pp. 405-411.
Nocito et al., Tungstate reduces the expression of gluconeogenic enzymes in STZ rats, PLoS One, Aug. 2012, vol. 7, Issue 8, p. e42305.
Osterburg et al., Sodium tungstate (Na2WO4) exposure increases apoptosis in human peripheral blood lymphocytes, J Immunotoxicol, Jul. 2010, vol. 7, Issue 3, pp. 174-182.
Paglia et al., The effects of local vanadium treatment on angiogenesis and chondrogenesis during fracture healing, J Orthop Res, Dec. 2012, vol. 30, Issue 12, pp. 1971-1978.
Park et al., Local insulin therapy affects fracture healing in a rat model, J Orthop Res, May 2013, vol. 31, Issue 5, pp. 776-782.
Patlolla et al., Solvent-dependent properties of electrospun fibrous composites for bone tissue regeneration, Acta Biomater, Jan. 2010, vol. 6, Issue 1, pp. 90-101.
Phornohutkul et al., The role of insulin in chondrogenesis, Mol Cell Endocrinol, Apr. 2006, vol. 249, Issue 1-2, pp. 107-115.
Pittenger et al., Multilineage potential of adult human mesenchymal stem cells, Science, Apr. 1999, vol. 284, Iss. 5411, p. 143-7.
Rizza et al., Dose-response characteristics for effects of insulin on production and utilization of glucose in man, American Journal of Physiology, Jun. 1981, vol. 240, Issue 6, pp. E630-E639.
Rodriguez-Gallardo et al., Effects of sodium tungstate on insulin and glucagon secretion in the perfused rat pancreas, Eur J Pharmacol, Aug. 2000, Issue 402, Issues1-2, pp. 199-204.
Roos et al., Osteoarthritis of the Knee after Injury to the Anterior Cruciate Ligament or Meniscus: The Influence of Time and Age, Osteoarthritis and Cartilage, Dec. 1995, vol. 3, Issue 4, pp. 261-267.
Selmi et al., Autologous chondrocyte implantation in a novel alginate-agarose hydrogel: outcome at two years, J Bone Joint Surg Br, May 2008, vol. 90(5), pp. 597-604.
Shanmugasundaram et al., Microscale versus nanoscale scaffold architecture for mesenchymal stem cell chondrogenesis, Tissue Eng Part A, Mar. 2011, vol. 17(5-6), pp. 831-840.
Taylor, 9 Therapeutic uses of trace elements, Clin Endocrinol Metab, Aug. 1985, vol. 14, Issue 3, pp. 703-724.

* cited by examiner

SYSTEM AND METHOD FOR INSULIN-MIMETIC OF CARTILAGE, BONE, OR OSTEOCHONDRAL REPAIR AND PIEZOELECTRIC COMPOSITE SCAFFOLD

CROSS-REFERENCE TO RELATED APPLICATION

The present application claims the benefit of the filing date of U.S. Provisional Patent Application No. 62/401,979, filed Sep. 30, 2016, and Provisional Patent Application No. 62/402,064, also filed Sep. 30, 2016, the disclosures of which are hereby incorporated herein by reference.

STATEMENT REGARDING FEDERALLY SPONSORED RESEARCH

This invention was made with government support under Contract No. DMR-1006510 and DMR-1610125 awarded by the National Science Foundation. The government has certain rights in this invention.

FIELD OF USE

The present disclosure generally relates to the use of an insulin-mimetic alone or in combination with a scaffold for cartilage tissue engineering applications. In particular, the present disclosure relates to the effect of an insulin-mimetic on mesenchymal stem cells for cell growth, attachment, differentiation and/or tissue repair and the use of an insulin-mimetic in supporting cartilage repair and a biodegradable composite scaffold containing a piezoelectric material for cell growth, attachment, differentiation and/or tissue repair.

BACKGROUND

Articular cartilage has limited ability to regenerate and repair [1,2]. Current therapies do not restore a normal hyaline cartilage [3]. Osteoarthritis (OA) affects 27 million adults in the United States and the number is anticipated to rise to 67 million by 2030 [4]. Knee and hip replacements cost almost $42.3 billion in 2009 [4]. With OA beginning at about age 45 and early onset OA developing within 10 years of a major joint injury [5], there is a growing need for an effective treatment to repair articular cartilage.

Conventional approaches in tissue engineering and regenerative medicine utilize cells and/or growth factors in combination with biomaterial scaffolds to repair tissues. Mesenchymal stem cells (MSCs) derived from adult bone marrow are of great interest as a cell type due to their proliferative capacity and their ability to differentiate into multiple lineages including bone and cartilage cells [1,6]. These cells are also being investigated in clinical trials for cartilage repair [7] using liver and pancreas tissues.

Different approaches have been used to stimulate chondrogenesis and bone growth such as the use of transforming growth factor beta (TGF-β), bone morphogenetic protein (BMP) [8,9] and insulin and insulin-like growth factors (IGF) [10]. IGF-1 is involved in MSC chondrogenesis by stimulating proliferation, regulating apoptosis and inducing differentiation [10]. Insulin is structurally similar to IGF-1 whereby it can bind to the IGF-1 receptor and stimulate extracellular matrix (ECM) production [11].

Previous studies have found that systemic insulin treatment increased cell proliferation, soft callus formation/chondrogenesis, biomechanical properties and callus bone content in diabetes mellitus rats [12]. Furthermore, local administration of insulin has been found to improve healing and bone regeneration in animal models [13,14].

However, insulin is difficult to deliver locally due to its high molecular weight (51 amino acids and 5808 Da molecular weight (MW)) and stability; insulin goes through hydrolysis/degradation or intermolecular transformation during storage and use [15]. Moreover, increasing the insulin level in normal patients is not an option because of the risk of hypoglycemia. Therefore, insulin-mimetics have been sought.

In addition, the general approach to the use of tissue engineering in the repair and/or regeneration of tissue is to combine cells and/or biological factors with a biomaterial that acts as a scaffold for tissue development. The cells should be capable of propagating on a scaffold and acquiring the requisite organization and function to produce a properly functioning tissue, cartilage, bone, or both cartilage and bone.

Electrical stimulation is known to promote cellular growth. However there is a problem with electrical stimulus needing external power sources or batteries that can cause negative patient implications, and is cumbersome for the user.

Thus there still remains a need for innovative technologies for tissue engineering of inherently complex tissues, and in particular, musculoskeletal connective tissue such as cartilage and/or bone without the above drawbacks. Furthermore there also remains a need in the art for compositions and methods that are capable of inducing bone and/or cartilage growth and repair.

SUMMARY OF THE INVENTION

The present disclosure overcomes the problems of current state of the art and provides many more benefits. Disclosed are compositions and methods useful for promoting the growth and/or differentiation and/or repair of a cell and/or tissue. In certain aspects, the present disclosure provides an insulin-mimetic for facilitating growth, differentiation, and/or repair of a cell and/or a tissue and/or bone. Locally applied insulin and small molecule insulin-mimetics can enhance fracture healing.

In one embodiment, the insulin mimetic is sodium tungstate ($Na_2WO_4$). Sodium tungstate can be used alone or in combination with a scaffold. $Na_2WO_4$ was utilized as an inductive factor to enhance human mesenchymal stem cell (MSC) chondrogenesis. MSCs were also seeded onto three-dimensional (3-D) electrospun scaffolds in growth medium (GM), chondrogenic induction medium containing insulin (CCM) and CCM without insulin. $Na_2WO_4$ was added to the media leading to final concentrations of 0, 0.01, 0.1 and 1 mM.

Chondrogenic differentiation was assessed by biochemical analyses, immunostaining and gene expression. Cytotoxicity using human peripheral blood mononuclear cells (PBMCS) was also assessed. The chondrogenic differentiation of MSCs was enhanced in the presence of low concentrations of $Na_2WO_4$ as compared to control, without $Na_2WO_4$. $Na_2WO_4$ has piezoelectric properties.

In induction medium containing insulin, cells in 0.01 mM $Na_2WO_4$ produced significantly higher sulfated glycosaminoglycans, collagen type II and chondrogenic gene expression than all other groups at day 28. Cells in 0.1 mM $Na_2WO_4$ had significantly higher collagen II production and significantly higher sox-9 and aggrecan gene expression as compared to control at day 28. Cells in growth medium and induction medium without insulin containing low concentrations of $Na_2WO_4$ also expressed chondrogenic markers. $Na_2WO_4$ did not stimulate PBMC proliferation or apoptosis. The results demonstrate that $Na_2WO_4$ enhances chondrogenic differentiation of MSCs, does not have a toxic effect, and is useful for MSC-based approaches for cartilage repair.

In addition, compositions and methods described herein are useful for promoting the growth and/or differentiation and/or repair of a cell and/or tissue. In certain aspects, the present disclosure provides an electroactive, or piezoelectric, biomaterial as an electroactive scaffold for facilitating growth, differentiation, and/or repair of a cell and/or a tissue, including osteochondral repair. The use of piezoelectric biomaterials in tissue engineering scaffolds and medical devices allow for electrical stimulus without external power sources or batteries.

Piezoelectric materials act as highly sensitive mechanical-electrical transducers that will generate charges in response to minute vibrational forces. Piezoelectric scaffolds demonstrate electrical activity in response to minute mechanical deformation.

In another embodiment, the present disclosure illustrates a composite scaffold capable of supporting cell and tissue growth that may or may not include zinc oxide (ZnO), which has piezoelectric properties. In a particular embodiment, zinc oxide was fabricated into a flexible 3-D fibrous scaffold by embedding zinc oxide nanoparticles into a slow degrading polycaprolactone (PCL) fiber. When an inductive agent, such as sodium tungstate ($Na_2WO_4$), is utilized with the scaffold, it was determined in the present disclosure that a range of 0.01-5 weight (wt.) % sodium tungstate in the scaffold promoted excellent cell and tissue growth results and cytocompatibility results. These results may be utilized for promotion of cartilage, bone or both cartilage and bone repair.

Any combination and/or permutation of the embodiments are envisioned. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

To assist those of skill in the art in making and using the disclosed systems and methods, reference is made to the accompanying figures, wherein.

DETAILED DESCRIPTION

Figure 1A:
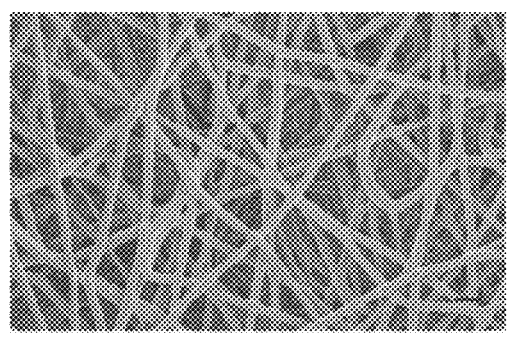
FIG. 1a is a scanning Electron Microscope (SEM) image of a poly (ε-caprolactone) (PCL) scaffold at 1000× magnification, scale bar=20 µm.

In general, this disclosure overcomes the disadvantages of past attempts. Shown is a novel use of an insulin mimetic and a piezoelectric composite scaffold in combination or alone for supporting cell, tissue, and bone growth. In one embodiment, the insulin mimetic is sodium tungstate ($Na_2WO_4$). While the use of sodium tungstate is exemplary, it will be understood that other insulin mimetics could be used. The amount of sodium tungstate could vary depending on the properties desired.

Sodium tungstate ($Na_2WO_4$) is a water soluble inorganic compound that can exert an insulin-like effect in diabetes [16,17]. Several studies have shown that oral administration of $Na_2WO_4$ into animal models of type 1 and type 2 diabetes normalize glycaemia without hypoglycemia [17-19]. Dominguez et al. [20] showed that glycogen synthesis and deposition are increased in the presence of $Na_2WO_4$. $Na_2WO_4$ stimulates insulin secretion and regenerates the β cell population however, it does not stimulate insulin secretion at low glucose levels suggesting that $Na_2WO_4$ does not induce hypoglycemia [21]. Moreover, $Na_2WO_4$ stimulates extracellular signal-regulated kinases (ERK) phosphorylation in different cell types [22,23]. ERK activation is important for MSC chondrogenesis [24,25]. Moreover, the molecular weight of $Na_2WO_4$ (293.82 g/mol or Da) is substantially lower than insulin which may facilitate transport via diffusion to the tissue. Depending on the implementation, $Na_2WO_4$ may be delivered locally to accelerate MSC-based approaches in cartilage repair.

The present disclosure discusses the effect of $Na_2WO_4$ on MSC chondrogenesis. The results show that $Na_2WO_4$ enhances MSC chondrogenesis. MSC chondrogenic differentiation was used with varying amounts of $Na_2WO_4$ using biochemical analysis, immunostaining, gene expression and collagen type II production. Testing was conducted on a three-dimensional (3-D) fibrous scaffold with fiber diameters and interfiber spacing in the micron-size range, which has been shown to support chondrogenesis [26]. Tissue engineering scaffolds were used for MSC chondrogenesis because they are widely used for growing cartilage in vitro, mimic the 3-D structure of the extracellular matrix, and are used clinically for cartilage repair [27,28]. Testing showed the effect of $Na_2WO_4$ on chondrogenic differentiation of human MSCs. Cytotoxicity of $Na_2WO_4$ was also tested. Peripheral blood mononuclear cells (PBMCs) were challenged with different concentrations of $Na_2WO_4$. Cell proliferation and viability were used to analyze the effect of $Na_2WO_4$ on PBMCs.

The materials and the methods of the present disclosure used in one embodiment will be described below. While this embodiment discusses the use of specific compounds and materials, it is understood that the method could be employed using similar materials. Similar quantities or measurements may be substituted without altering the method embodied below.

Scaffold Fabrication

In one embodiment, 15 wt. % poly (ε-caprolactone) (PCL, [(CH2)5COO]$_n$-, 80,000 MW, Sigma-Aldrich, Inc., St. Louis, Mo., USA) was dissolved in methylene chloride. This solution was electrospun to form a nonwoven fibrous scaffold [29]. The electrospinning setup included a syringe pump operating at 5 ml/h, 12 gauge needle, a high voltage source ranging from 20-25 kV and a grounded collector. The electrospun PCL scaffolds were characterized by scanning electron microscopy (SEM) using a LEO 1530 Gemini (Germany) instrument. SEM images were used to determine fiber diameters and inter-fiber spacing using Image J software (National Institutes of Health, USA) [29].

Cells

Peripheral blood was obtained from four healthy subjects, two males and two females (ages 18-30 years old). Peripheral blood mononuclear cells (PBMCs) were isolated by Ficoll Hypaque (Sigma-Aldrich) gradient separation [30]. Human MSCs were obtained from human bone marrow aspirates (Lonza, Walkersville, Md., USA) from four healthy subjects, two males and two females, ages 18-30 years old, according to previously published protocols and cryopreserved before use [31]. Human MSCs were characterized for the expression of surface markers CD29, CD44, CD73, CD90, and CD105 and lack expression of CD14, CD34 and CD45 as determined by flow cytometry [32-34]. The differentiation potency was determined by the differentiation of MSCs into osteoblasts, adipocytes and chondrocytes in vitro [32,33]. For both PBMCs and MSCs, all experiments described were repeated per donor.

MSC Growth

MSCs were cultured on the scaffolds in the presence of $Na_2WO_4$ ($Na_2WO_4.2H_2O$, MW=329.85 g/mol; Sigma Aldrich) in the range of 0.01-50 mM to determine which concentrations supported cell growth. Before cell seeding, scaffolds were cut into 6 mm diameter disks using a biopsy punch (Integra Miltek, York, Pa.), sterilized in 100% ethanol for 20 minutes and were air dried overnight. Cryopreserved MSCs were thawed and expanded in tissue culture treated polystyrene flasks (Nunc, Thermo Fisher Scientific, Waltham, Mass., USA) in growth medium (GM) comprised of Dulbecco's Modified Eagle's Medium (DMEM, Invitrogen, Grand Island, N.Y., USA), 10% fetal bovine serum (Hyclone, Thermo Fisher Scientific) and 1% antibiotic-antimycotic (Invitrogen) at 37° C. and 5% $CO_2$ until 70-80% confluent. Cells were trypsinized using 0.25% Trypsin-EDTA (Thermo Fisher Scientific), resuspended in GM and then seeded onto scaffolds at $3.5 \times 10^4$ cells/cm$^2$ and cultured for 11 days in GM alone or with $Na_2WO_4$. $Na_2WO_4$ was added to GM leading to final $Na_2WO_4$ concentrations of 0, 0.01, 0.1, 1, 10 and 50 mM. Samples (n=4) were harvested and analyzed at days 4, 7 and 11 for cell number using the PicoGreen® ds DNA assay (Life Technologies).

MSCs of known cell number were used as a standard. Standards and samples were prepared by lysing the cells using 0.1% Triton X-100 (Sigma-Aldrich, Mo., USA). The cell lysate of samples and standards (n=4 per group) was mixed with an equal volume of Pico Green dye, which binds to the double-stranded (ds) DNA. Fluorescence intensity was measured with a microplate reader ((FLX800, Biotek Instruments, Vt., USA)) at 480 nm excitation and 520 nm emission. A standard curve of known cell number was used to determine the sample cell number.

PBMC Proliferation Assay

The cytotoxicity of $Na_2WO_4$ was examined using PBMCs. Cell proliferation was measured using tritiated thymidine ($^3$H-TdR) incorporation as described in Kapoor et al. [35]. PBMCs were resuspended at $10^6$/mL in RPMI 640 (Sigma-Aldrich) and 10% fetal bovine serum (Hyclone, Thermo Fisher Scientific, Waltham, Mass., USA). Positive control cells were challenged with 1% phytohemagglutinin (PHA) (Gibco). The experimental groups were stimulated with 0.01, 0.1, and 1 mM $Na_2WO_4$. Baseline proliferation was studied in parallel cultures with medium alone or vehicle (1 µl DI $H_2O$). The assay was established with $2 \times 10^5$ PBMC in 200 µL volume in a flat bottom 96-well tissue culture plate. Each experimental group was studied in triplicate cultures. After 48 hours at 37° C., each well was pulsed with 1 µCi/ml of $^3$H-TdR.

After 16 h, the cells were harvested on glass fiber filters (Cambridge Technology, Inc.) using a cell harvester (EMD Millipore). The filters were washed with ethanol and then air dried overnight. The radioactive incorporation of $^3$H-TdR in the cells was measured using a liquid scintillation counter (Beckman; Fullerton, Calif., USA). The stimulation index (SI) was calculated as disintegration per minute (dpm) of treated group/dpm of unstimulated PBMCs (0 mM).

Cell Titer Blue Assay

CellTiter-Blue Assay (Promega, Madison, Wis.) was used to assess the viability of PBMCs. Cell Titre Blue was used to measure the metabolic activity of PBMCs as a surrogate for cell number. Each experimental group was performed in triplicate in 96-well tissue culture plates. After 4 days, CellTiter-Blue reagent (20 µL/well) was added to each well. The plates were incubated and after 4 hours, the fluorescence intensity was measured with microplate reader (Synergy, HTX, BioTek, Winooski, Vt., USA) at 560/590 nm emission. Percent viability was calculated as the fluorescence reading of treated (stimulated) cells divided by untreated healthy cells, which were considered 100% viable as described in Greco et al. [36].

Chondrogenesis Culture and Characterization

Chondrogenesis Culture. Cryopreserved MSCs were thawed and expanded in GM until 70-80% confluent. Cells were trypsininzed and then seeded on 6 mm diameter scaffold disks at $1.76 \times 10^5$ cells/cm$^2$ and cultured for 28 days in GM, chondrogenic induction medium (CCM), or CCM without insulin, according to previously published methods [26]. CCM consisted of DMEM high glucose containing 4 mM L-glutamine (Invitrogen, Grand Island, N.Y., USA), 0.1 µM dexamethasone (Sigma-Aldrich), 0.17 mM ascorbic acid-2-phosphate (Wako Chemicals, Richmond, Va., USA), 1% ITS+(6.25 □g/mL insulin, 6.25 □g/mL transferrin, 6.25 ng/mL selenous acid, 5.35 µg/ml linoleic acid and 1.25 mg of bovine serum albumin) Premix Culture Supplement (Corning, Corning, N.Y., USA), 1× antibiotic-antimycotic, 1 mM sodium pyruvate (Sigma-Aldrich), 0.35 mM proline (Sigma-Aldrich), and 10 ng/mL recombinant human transforming growth factor-beta3 (TGF-β3, ProSpec, Israel). CCM without insulin consisted of CCM where the 1% ITS+Premix Culture Supplement was substituted with 1% stock solution (6.25 µg/ml transferrin and 6.25 ng/ml selenous acid, 5.35 µg/ml lionleic acid (Sigma-Aldrich) and 1.25 mg of bovine serum albumin (Fisher Scientific). $Na_2WO_4$ was added to all media leading to final $Na_2WO_4$ concentrations of 0, 0.01, 0.1 and 1 mM. Samples were harvested and analyzed for sulfated glycosaminoglycans (sGAG), cell number and gene expression at day 14 and 28 and for collagen type II and immunostaining at day 28.

Sulfated Glycosaminoglycan Production and Cell Number.

Production of sGAG and cell number were determined. Samples were digested using papain (Sigma-Aldrich, Mo., USA) buffer overnight at 65 C. ° following manufacturer's protocol. The sGAG assay is used to measure the total sulfated proteoglycan content using Blyscan sGAG Assay Kit (Biocolor, UK). Cell lysate of samples (n=4 per group) and color reagent were combined in transparent 96-well plate and the absorbance at 656 nm was measured using a microplate spectrophotometer (EMax, Molecular Devices, Melville, N.Y., USA). sGAG concentration was determined relative to chondroitin sulfate standard curve. PicoGreen® ds DNA assay (Life Technologies) was used to determine the cell number. MSCs of known cell number were used as standards. Standards were prepared by lysing the cells using papain buffer. The cell lysate of samples and standards (n=4 per group) was mixed with an equal volume of Pico Green reagent. Fluorescence intensity was measured with a microplate reader ((FLX800, Biotek Instruments, Vt., USA)) at 480 nm excitation and 520 nm emission. A standard curve of known cell number was used to determine the sample cell number. GAG production was normalized to cell number.

Gene Expression.

Gene expression was evaluated using quantitative reverse transcription (RT)-polymerase chain reaction (PCR) analysis. RT-PCR was performed with RNeasy Micro Kit and SYBR Green RT-PCR Kit (Qiagen; Valencia, Calif., USA) using the MX4000 detection system (Stratagene) according to the manufacturer's protocol. Relative gene expression of SOX-9, aggrecan and collagen type II were determined. Samples (n=4 per group) were harvested and digested using Lysis Buffer. RNA was isolated from the samples using RNeasy Micro Kit (Qiagen) including DNA digestion step (RNase Free DNase Set; Qiagen). The RNA quantity and integrity were determined by measuring the absorbance at 260 nm and the absorbance ratio of 260 nm/280 nm, respectively, using Nanodrop™ Spectrophotometer (Thermo Fisher Scientific). Quantitative PCR analysis was performed using QuantiTect SYBR Green supermix including the QuantiTect Primer Assays. The reverse transcription step ran for 30 minutes at 50° C., 15 minutes at 95° C. of PCR activation followed by forty cycle of amplification consisting of 15 s denaturation at 94° C., 30 s of annealing at 55° C., and 30 s of extension at 72° C. A melting curve analysis of the RT-PCR product was included for each reaction. Samples were analyzed in triplicate and the value of each gene was normalized to the reference gene ribosomal protein, large, P0 (RPLP0) for the same sample ($\Delta C_T$). Primers were purchased from Qiagen (Hs_ACAN, QT00001365; Hs_SOX9, QT00001498; Hs_COL2A1, QT00049518; and Hs_RPLP0 QT00075012).

Immunostaining.

Immunostaining was used to observe cell morphology and collagen type II deposition at day 28. Samples were fixed using 4% paraformaldehyde for 20 minutes. Samples were permealized with 0.1% Triton-X for 15 minutes and then non-specific binding was blocked using 5% donkey serum (Sigma-Aldrich, Mo., USA) for 1 hour. Samples were incubated with mouse antihuman collagen type II antibody (EMD Millipore; Calif., USA) in 4° C. overnight. Samples were then incubated with conjugated northern light 493 secondary antibody (Donkey anti-Mouse IgG, Fisher Scientific, Rockford, Ill.) and rhodamine phalloidin (Life Technologies) for actin filament for 1 h. The nucleus was stained with 4′,6-diamidino-2-phenylindole (DAPI, Fisher Scientific). The images were taken using a confocal fluorescence microscope (C1-si, Nikon, Japan).

Collagen Type II ELISA.

Collagen type II production was quantified by enzyme-linked immunosorbent assay (ELISA) using a collagen type II detection kit (Chondrex Inc. Redmond, Wash., USA). The ELISA was conducted following the manufacturer's instructions. Briefly, samples (n=4 per group) were harvested at day 28 and washed with PBS. Collagen was digested by adding pepsin solution (0.1 mg/ml in 0.05 M acetic acid) at 4 C° for two days with gentle mixing. The digested samples were centrifuged for 3 minutes and supernatants were collected. Pancreatic elastase was added to the samples and incubated overnight at 4° C. Supernatants were then collected. The ELISA plate which was coated with collagen type II was prepared as described by the manufacturer and the absorbance at 490 nm was measured using a microplate spectrophotometer (Emax, Molecular Devices). The collagen type II production was determined relative to the standard curve.

Statistical Analysis

Statistical analysis was performed using one-way and two-way analysis of variance (ANOVA) and the post hoc Tukey's HSD for statistical differences (using SPSS software). Prior analysis, Shapiro-Wilk test was used to test the normality and Levene's test for equal variance. Probability (p) values<0.05 were considered statistically significant. Two-way ANOVA was used for analyzing cell number, sGAG, gene expression while one-way ANOVA was used for analyzing PBMCs viability and collagen type II ELISA.

Results

Scaffolds

As shown in FIG. 1a, the three-dimensional fibrous PCL scaffolds had fiber diameters and interfiber spacing in the micron-size range. The fiber diameter and interfiber spacing were 5.7±0.9 μm and 48±14 μm, respectively.

MSC Growth

Figure 1B:
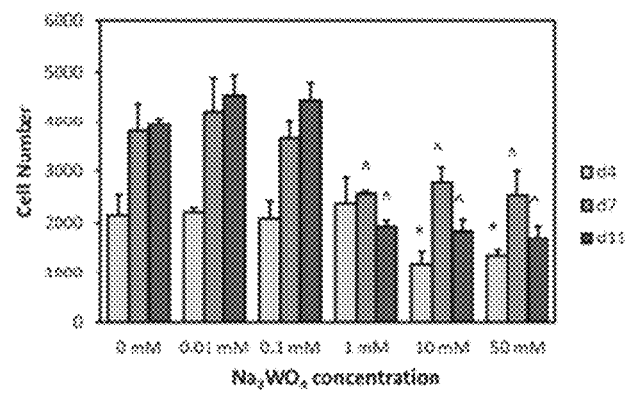
FIG. 1b is a chart showing cell number as detected by DNA content at days 4, 7 and 11 on scaffolds in growth medium (GM) with different concentrations of sodium tungstate ($Na_2WO_4$), where values are Mean±standard deviation (S.D.) and (n=4) and $\hat{0}p<0.05$, significantly lower than 0, 0.01 and 0.1 mM groups at time point, and where *$p<0.05$, significantly lower than 0, 0.01, 0.1, and 1 mM groups at time point.

Referring to FIG. 1b, to determine which concentrations of $Na_2WO_4$ could support cell growth, MSCs were cultured on the scaffolds in GM. 0, 0.01, and 0.1 mM $Na_2WO_4$ groups significantly increased in cell numbers from days 4 to 7 (p<0.05). 1, 10 and 50 mM $Na_2WO_4$ groups had significantly lower cell numbers as compared to the other groups at days 7 and 11 (p<0.05 and p<0.001 respectively). Other concentrations such as 0.01, 0.1 and 1 mM $Na_2WO_4$ were chosen for further investigation. Depending on the implementation various concentrations could also be investigated. However cyto-toxicity may be a concern with higher concentrations.

PBMCs Proliferation and Viability

Figure 2A:
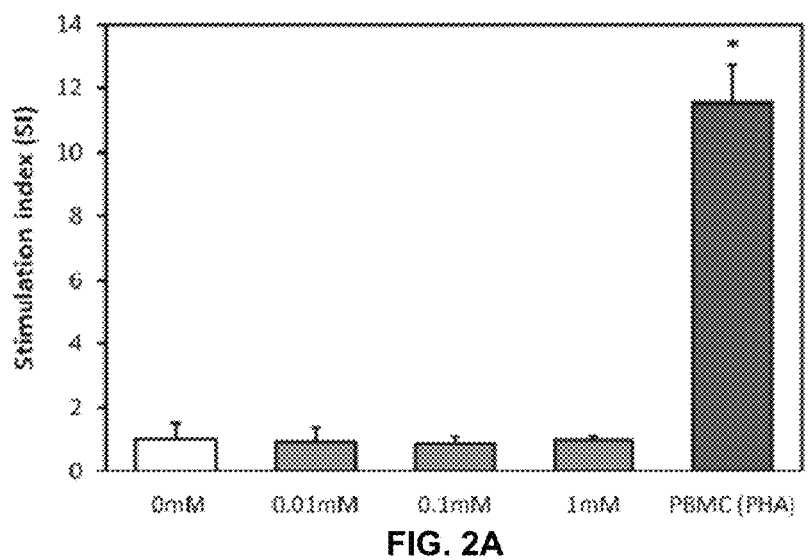
FIG. 2a is a chart showing proliferative response of $Na_2WO_4$ on peripheral blood mononuclear cells (PBMCs), stimulation index (SI) is calculated as disintegration per minute (dpm) of treated group/dpm of unstimulated PBMCs (0 mM)
Figure 2B:
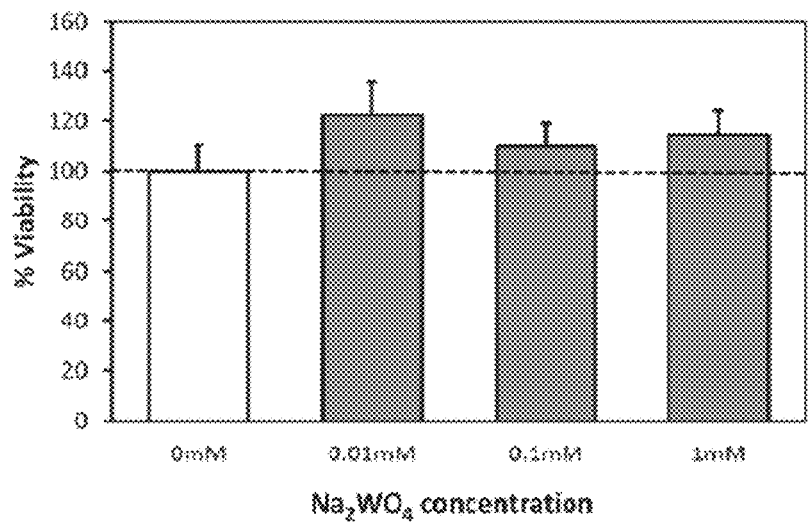
FIG. 2b is a chart showing proliferative response of $Na_2WO_4$ on peripheral PBMCs, percent viability of PBMCs using CellTiter blue after 4 days of exposure to $Na_2WO_4$, where the proliferative values are presented as Mean S.I.±S.D, and percent viability is represented as Mean±S.D. (n=3), and *$p<0.05$, significantly higher than all other groups, phytohemagglutinin (PHA)

The cytotoxicity of $Na_2WO_4$ was evaluated using PBMCs as a surrogate for untoward effects on the immune system. PBMC proliferation and viability studies were performed by stimulating with varying amounts of $Na_2WO_4$ (0.01, 0.1 and 1 mM). The experimental system was evaluated by stimulating with a T-cell mitogen, PHA. The results indicated no significant difference in cell proliferation with different concentrations of $Na_2WO_4$. As shown in FIG. 2a, the SIs, which was calculated as the proliferation of stimulated PBMCs over unstimulated PBMCs, were approximately 1 for all $Na_2WO_4$ groups. The PBMC proliferation in the presence of $Na_2WO_4$ was comparable to that achieved in the absence of $Na_2WO_4$. While activating the PBMCs with mitogen, PHA increased the SI significantly (11.5±1.2), as shown in the chart of FIG. 2a. Cell viability assay was used to ensure the cells did not undergo apoptosis. No significant differences in cell viability between groups with $Na_2WO_4$ and without (0 mM) were detected, as shown in FIG. 2b. Hence the biocompatibility in the presence of the concentration of sodium tungstate between 0.01 mM to 0.1 mM is comparable to the absence of the sodium tungstate.

Chondrogenic Differentiation

Figure 3A:
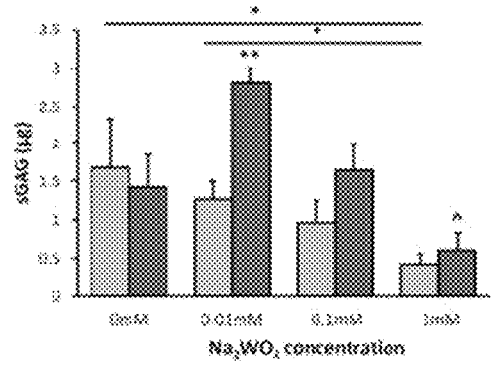
FIGS. 3a-c are charts showing sulfated glycosaminoglycan (sGAG) production and mesenchymal stem cell (MSC) number on varying concentrations of $Na_2WO_4$ in chondrogenic induction medium (CCM) at days 14 and 28 where the figures are a) sGAG production, b) cell number, and c) normalized sGAG to cell number, and values are Mean±S.D and (n=4), and *$p<0.05$, significant difference between the two groups, and **$p<0.05$, significantly higher as compared with all groups at time point, and $\hat{0}p<0.05$, significantly lower as compared with all groups at specific time point.
Figure 3B:
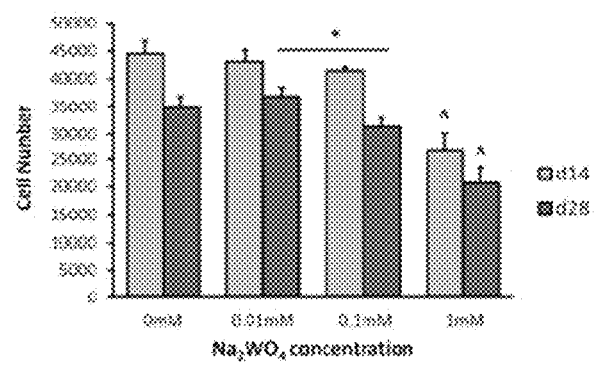
Figure 3C:
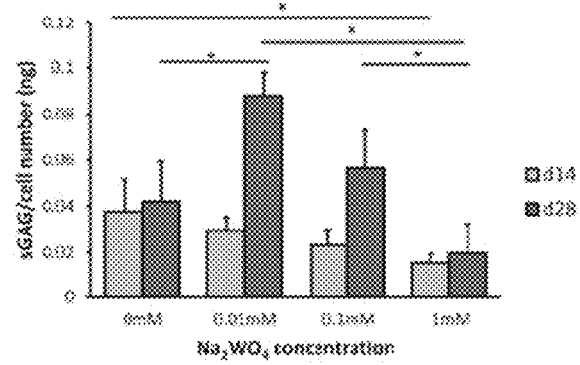

To determine the effect of $Na_2WO_4$ on chondrogenic differentiation of MSCs, sGAG production was determined at days 14 and 28 as shown in FIG. 3a. Cells in 0.01 mM $Na_2WO_4$ group had higher sGAG production than all other groups at day 28 (p<0.005) in CCM. In addition, a significant increase in sGAG production occurred between days 14 and 28 for 0.01 mM $Na_2WO_4$ group in CCM. Overall sGAG production in GM was less than in CCM, however it was significantly higher in 0.1 mM $Na_2WO_4$ in GM as compared to GM alone at day 14, as shown in FIGS. 6a-6d. The corresponding cell number was determined as shown in FIG. 3b. Cell number was significantly lower for the 1 mM $Na_2WO_4$ group as compared to other groups in CCM. Cell number in 0.01 mM $Na_2WO_4$ was significantly higher than 0.1 mM at day 28 (p<0.05) in CCM. Cell number in GM was significantly higher with the addition of 0.1 mM $Na_2WO_4$ than 0 mM at day 14, as shown in FIGS. 6a-6d. Referring to FIG. 3c, normalized sGAG to cell number was significantly higher for 0.01 mM $Na_2WO_4$ as compared to 0 and 1 mM groups (p<0.05) in CCM at day 28. sGAG production in 0.01 and 0.1 mM $Na_2WO_4$ was higher than 0 mM group in CCM without insulin but not significantly, as shown in FIGS. 6a-6d. There were significantly lower cell numbers and sGAG in 1 mM $Na_2WO_4$ as compared to all other groups at day 28, and significantly lower normalized sGAG to cell number for 1 mM as compared to 0.01 mM at day 28 in CCM without insulin.

Figure 4A:
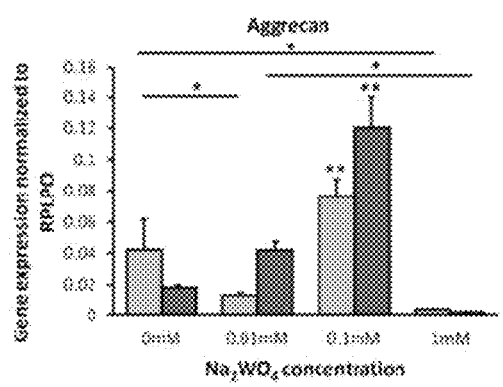
FIGS. 4a-c are charts showing gene expression for mesenchymal stem cells (MSCs) on scaffolds with varying amounts of $Na_2WO_4$ in CCM at days 14 and 28 where the figures are (a) aggrecan, (b) SOX-9 and (c) collagen type II, and values are Mean±S.D, and (n=4), and *$p<0.05$, significant difference between the two groups, and **$p<0.05$, significantly higher as compared with all groups at time point, and $\hat{0}p<0.05$, significantly lower as compared with all groups at specific time point, and RPLPO (ribosomal protein, large, PO): reference gene.
Figure 4B:
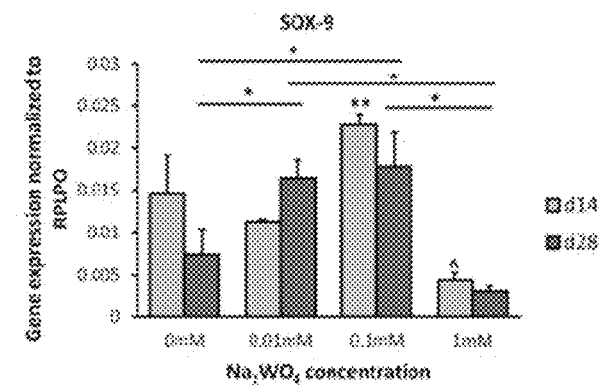
Figure 4C:
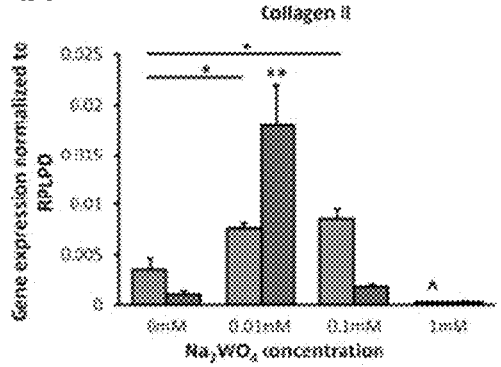
Figure 7A:
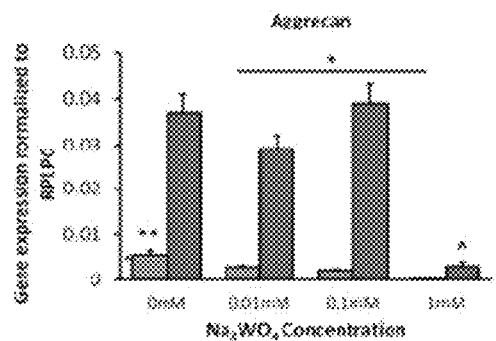
FIGS. 7a-c are charts showing gene expression for mesenchymal stem cells (MSCs) on scaffolds with varying amounts of $Na_2WO_4$ in growth medium (GM) at days 14 and 28, where the figures are (a) aggrecan, (b) SOX-9 and (c) collagen type II, and values are Mean±S.D. (n=4). *$p<0.05$, significant difference between two groups, and **$p<0.05$, significantly higher as compared with all groups at time point, and $\hat{0}p<0.05$, significantly lower as compared with all groups at specific time point, and RPLPO (ribosomal protein, large, PO): reference gene.
Figure 7B:
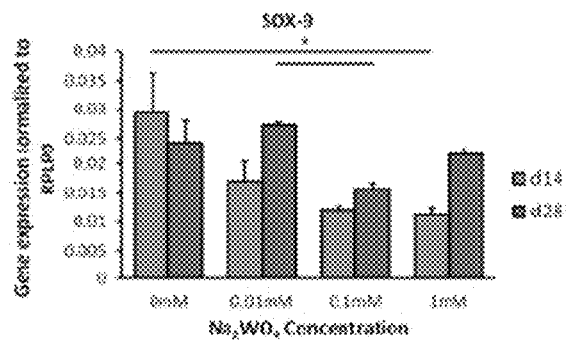
Figure 7C:
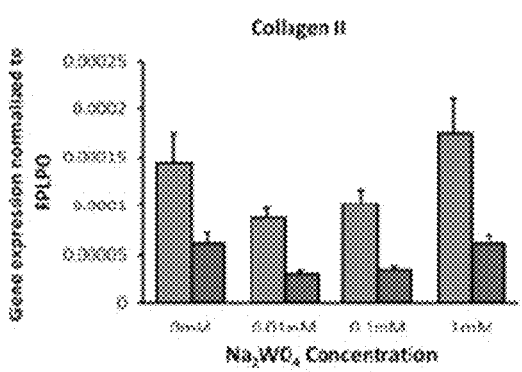
Figure 8A:
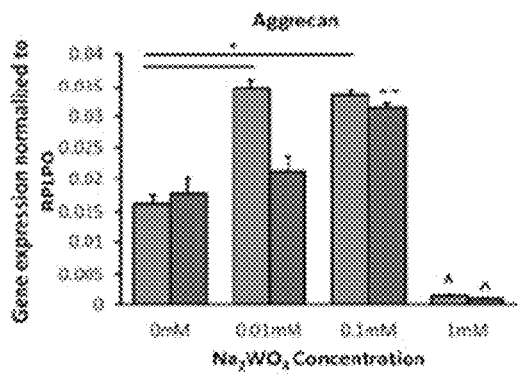
FIGS. 8a-c are charts showing gene expression for mesenchymal stem cells (MSCs) on scaffolds with varying amounts of $Na_2WO_4$ in chondrogenic induction medium (CCM) without insulin at days 14 and 28 where the Figures are (a) aggrecan, (b) SOX-9 and (c) collagen type II and values are Mean±S.D. (n=4), where *p<0.05, significant difference between two groups, where **p<0.05, significantly higher as compared with all groups at time point and ôp<0.05, significantly lower as compared with all groups at specific time point.
Figure 8B:
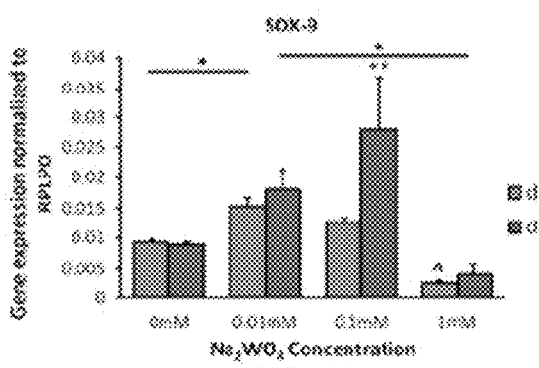
Figure 8C:
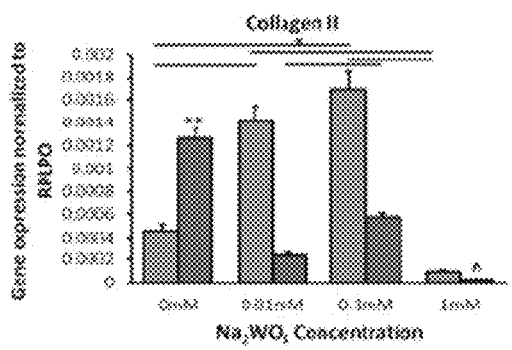
Figure 10:
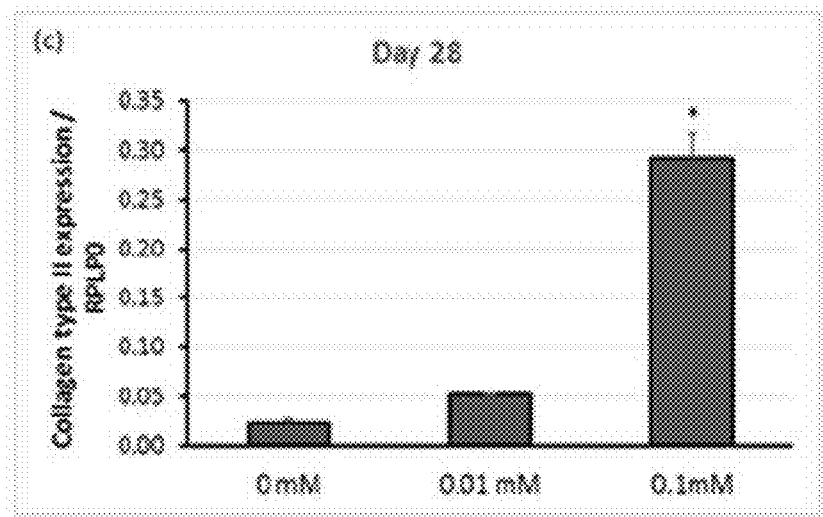
FIG. 10 is a chart showing gene expression for collagen type II.
Figure 11:
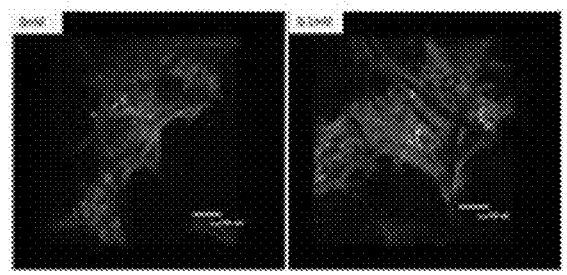
FIG. 11 are confocal microscopy images of MSCs cultured on scaffolds with varying concentrations of ST in chondrogenic medium for 28 days, and F-Actin red, collagen II green and nucleus blue, 40× objective.

Gene expression for chondrogenic markers was evaluated at days 14 and 28. Aggrecan gene expression was significantly higher in the 0.1 mM $Na_2WO_4$ group as compared to all groups at days 14 and 28 in CCM (p<0.05 and p<0.001 respectively, as shown in FIG. 4a.). Cells in 0.01 mM $Na_2WO_4$ expressed lower aggrecan expression as compared with 0 mM at day 14 (p<0.05). Cells in 0.1 mM $Na_2WO_4$ had the highest SOX-9 gene expression at day 14 (p<0.05), as shown in FIG. 4b. Also, cells in 0.01 and 0.1 mM expressed significantly higher SOX-9 as compared with 0 mM $Na_2WO_4$ (p<0.05 and p<0.01, respectively) at day 28. Cells in 0.01 and 0.1 mM $Na_2WO_4$ expressed significantly higher collagen type II as compared with 0 mM at day 14 (p<0.001 and p<0.001 respectively, as shown in FIG. 4c). By day 28, collagen type II gene expression was significantly higher for 0.01 mM $Na_2WO_4$ as compared to all groups in CCM (p<0.001). A significant increase in collagen type II expression was detected between days 14 and 28 for cells in 0.01 mM in CCM. Cells in 1 mM $Na_2WO_4$ exhibited the lowest gene expression for all genes in CCM. For cells cultured in CCM without insulin, gene expression for aggrecan and collagen type II was significantly higher in 0.01 and 0.1 mM $Na_2WO_4$ as compared with 0 and 1 mM groups at days 14 and 28, as shown in FIGS. 8a-8c. Also, SOX-9 gene expression was significantly higher in 0.01 mM as compared to 0 mM at day 14 in CCM without insulin, as shown in FIGS. 8a-8c. With reference to FIGS. 7a-7c, there was no significant upregulation of chondrogenic genes in GM with $Na_2WO_4$. FIG. 10 is a chart showing gene expression for collagen type II.

Figure 5A:
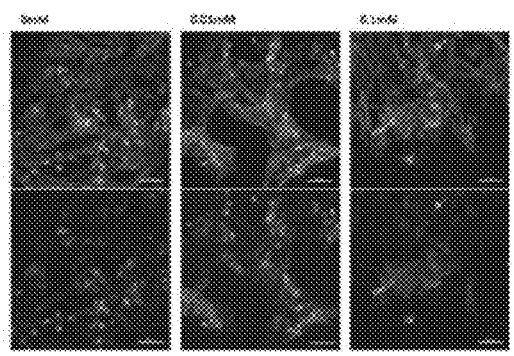
FIG. 5a are confocal microscopy images of mesenchymal stem cells (MSCs) seeded on scaffolds with varying concentrations of $Na_2WO_4$ and collagen type II production as detected by ELISA using varying concentrations of $Na_2WO_4$ in CCM at day 28, where the figures are (a) Immunofluorescent staining for Type II collagen (green), actin filaments (red), and nucleus (blue) are shown, and the scale bar=50 µm.

The cell morphology and collagen type II immunostaining staining on scaffolds with different concentrations of $Na_2WO_4$ were evaluated using confocal microscopy at day 28 as shown in FIG. 5a. $Na_2WO_4$ groups in CCM appeared to show more intense collagen type II staining as compared with 0 mM. Collagen type II staining appeared to exhibit a punctate staining pattern, which is suggestive of intracellular localization. All groups had intense actin filament staining as an indicator of attachment. Moreover, collagen type II staining appeared to be more intense in 0.01 and 0.1 mM $Na_2WO_4$ in GM as compared with 0 mM, where there was no staining CCM without insulin groups, except for 1 mM $Na_2WO_4$, showed collagen type II staining and intense actin staining (images not shown).

Figure 5B:
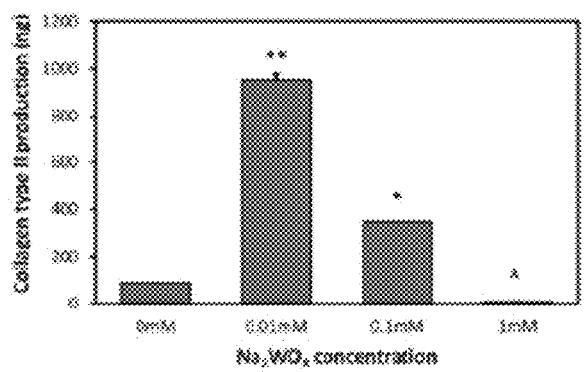
FIG. 5b is a chart showing collagen type II production where values are Mean±S.D. (n=4), and *$p<0.05$, significantly higher as compared to 0 mM and 1 mM, and **$p<0.05$, significantly higher as compared with all groups, and $\hat{0}p<0.05$ significantly lower as compared with all groups.
Figure 6A:
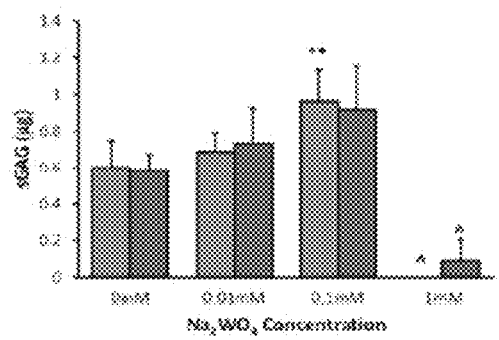
FIGS. 6a-d are charts showing sulfated glycosaminoglycan (sGAG) production and mesenchymal stem cell (MSC) number on varying concentrations of $Na_2WO_4$ in growth medium (GM) or chondrogenic induction medium (CCM) without insulin at days 14 and 28, where the figures are a) sGAG production in GM, b) cell number in GM, (c) sGAG production in CCM without insulin and (d) cell number in CCM without insulin, and values are Mean±standard deviation (S.D.). (n=4). *$p<0.05$, significant difference between two groups, and **$p<0.05$, significantly higher as compared with all groups at time point, and $\hat{0}p<0.05$, significantly lower as compared with all groups at specific time point.
Figure 6B:
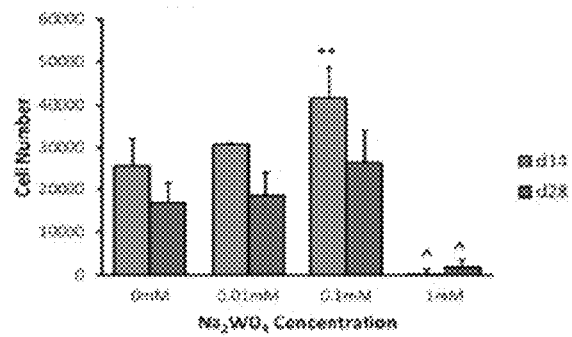
Figure 6C:
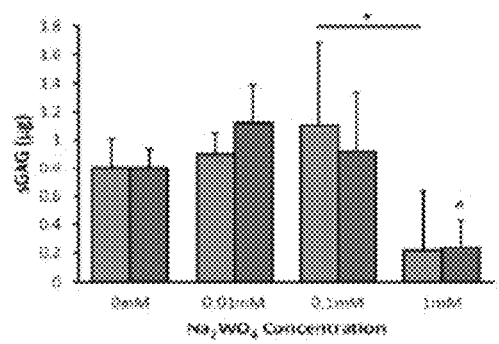
Figure 6D:
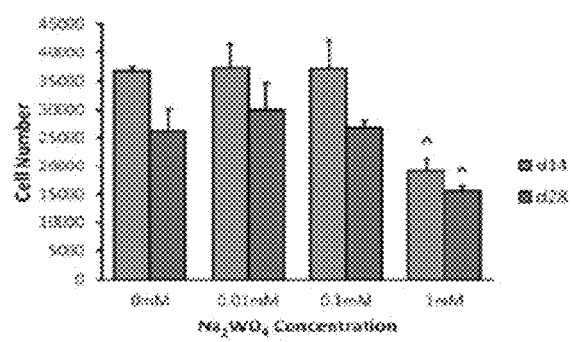
Figure 9:
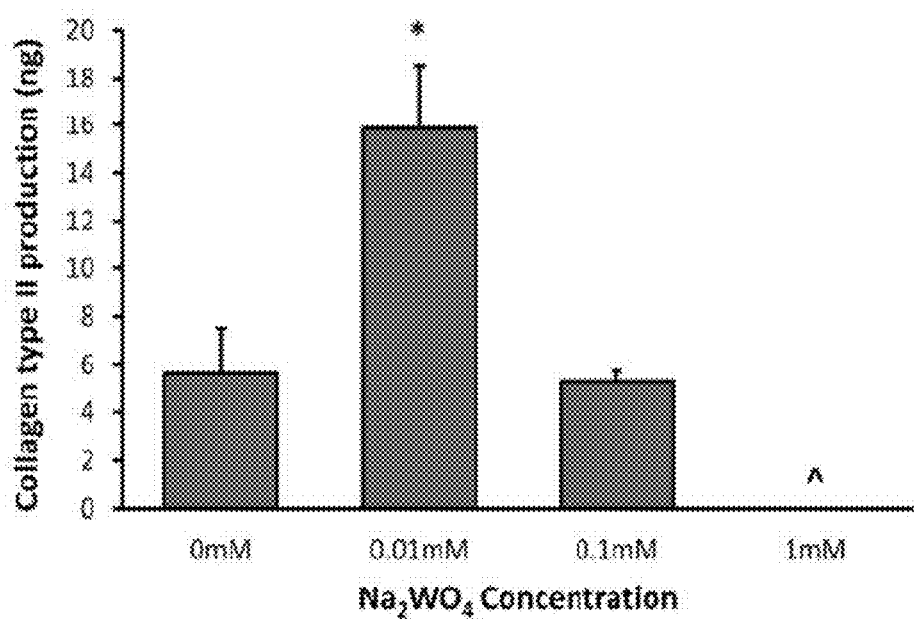
FIG. 9 is a chart showing collagen type II production as detected by ELISA using varying concentrations of $Na_2WO_4$ in growth medium (GM) at day 28 where values are Mean±S.D. *p<0.05, significantly higher as compared with all groups, and ôp<0.05 significantly lower as compared with all groups.

Referring to FIG. 5b, collagen type II production was determined for all groups at day 28 in CCM by ELISA. Cells cultured in 0.01 mM $Na_2WO_4$ produced the highest collagen type II (p<0.001) as compared to all other groups. Cells cultured in 0.1 mM $Na_2WO_4$ demonstrated significantly higher collagen type II production than without $Na_2WO_4$ (0 mM) and 1 mM $Na_2WO_4$ (p<0.001) and production of collagen type II was the lowest in 1 mM group (p<0.001). Furthermore, cells in the 0.01 mM group in GM produced significantly higher collagen type II as compared to 0 mM group (p<0.05), as shown in FIG. 9. Collagen type II production was not detected for CCM without insulin groups using the ELISA assay.

Discussion

The effect of $Na_2WO_4$ on MSC chondrogenesis was investigated for the first time in this disclosure. Low concentrations of $Na_2WO_4$ enhanced chondrogenic differentiation of MSCs in vitro, as indicated by higher expression of chondrogenic markers in comparison to cultures without the use of $Na_2WO_4$. Low concentrations of $Na_2WO_4$ also enhanced MSC growth and did not provoke a proliferative response in PBMCs, indicating $Na_2WO_4$ could be a potential therapeutic agent for MSC approaches in stimulating cartilage formation.

$Na_2WO_4$ has been investigated as insulin mimetic [37]. However this past investigation cited limited only in tissue such as liver, pancreas, and muscle but not in bone and cartilage as the present disclosure investigated. Insulin and IGF play important roles in cartilage and chondrogenic differentiation of MSCs. Insulin is an essential stimulator for chondrocyte proliferation [38] as well as MSC chondrogenesis [39]. Mueller et al. [39] demonstrated that chondrogenic differentiation of MSCs was not induced without insulin and chondrogenesis markers mainly GAG and collagen were increased by insulin in a dose dependent manner Local insulin delivery in diabetic bone fracture enhanced bone repair [40]. However, insulin treatment could lead to hypoglycemia. Moreover, it is difficult to control insulin delivery since it is a high molecular weight protein. $Na_2WO_4$ as a stable, low molecular weight material and an insulin mimetic may overcome these challenges.

The mechanism of action, safety, and efficacy of $Na_2WO_4$ have been demonstrated in preclinical animal diabetic models [37]. Similar to insulin, $Na_2WO_4$ can increase glycogen synthesis through activation of the ERK pathway [20]. However, Zafra et al. showed that $Na_2WO_4$ activates the ERK pathway independent of the insulin receptor using G-protein [41]. $Na_2WO_4$ also does not activate the IGF receptor and has not shown hypoglycemic action in preclinical or clinical studies [37]. ERK activation is involved in MSC chondrogenesis [24] and may be a part of the mechanism for the $Na_2WO_4$ effect on MSC chondrogenesis in this disclosure. MSC chondrogenesis was enhanced for low concentrations of $Na_2WO_4$ in complete induction medium containing insulin. Chondrogenic gene expression, aggrecan, sox-9 and collagen type II significantly increased as compared to control (without $Na_2WO_4$). Collagen type II and sGAG production was highest in the 0.01 mM group. Moreover, $Na_2WO_4$ enhanced the expression of chondrogenic markers in cultures without insulin, both in growth medium and induction medium without insulin.

Its effect was less pronounced than when combined with insulin, suggesting insulin may have a synergistic effect. For therapeutic strategies, the concentration of $Na_2WO_4$ may need to be optimized by examining additional concentrations of $Na_2WO_4$ between 0 to 0.1 mM and using media with lower concentrations of insulin that more closely mimic physiological levels [42]. $Na_2WO_4$ combined with low levels of insulin to avoid hypoglycemia may be an effective approach to promote MSC-based cartilage repair.

Although previous studies have been performed to investigate the toxicity of tungsten or $Na_2WO_4$ [43,44], it was determined that further tested was needed for the present disclosure. The concentration of $Na_2WO_4$ used to evaluate the anti-diabetic effect was around 6 mM [18,19]. Toxicity was not reported in animal studies [17,18,45] or in vitro [20] as an anti-diabetic agent. Moreover, $Na_2WO_4$ was studied in obese non-diabetic patients without any toxicity effect [46]. Our results demonstrate that low concentrations of $Na_2WO_4$ enhanced MSC proliferation while high concentrations of $Na_2WO_4$ significantly lowered MSC numbers. Moreover, low doses of $Na_2WO_4$ did not stimulate PBMC proliferation or apoptosis which suggests that low doses of $Na_2WO_4$ do not have a toxic effect. Our studies compliment findings by Osterburg et al., which investigated the effect of $Na_2WO_4$ on human peripheral blood lymphocytes in vitro. They demonstrated that at 1 mM dose, significant toxicity occurred while 0.01 mM and 0.1 mM $Na_2WO_4$ did not stimulate an immune response [47].

$Na_2WO_4$ as a water soluble, small molecule could be readily delivered to sites of injury via direct injection or incorporated in drug delivery or scaffolding devices. Metallic ions or compounds would be stable during implant processing allowing for a range of solvents, temperatures or pressures to be used [48]. They also are low cost in comparison to recombinant proteins and may have a higher safety [48]. Metallic ions can interact with other ions that can change cellular functions, activate signaling pathways or ion channels and bind to macromolecules such as enzymes or nucleic acids [49]. Increasing evidence has demonstrated the biological benefit of metallic ions releasing from implants. A biodegradable magnesium alloy has been studied for orthopedic applications [50] and has been shown to facilitate bone healing in clinical trials [51]. Furthermore, local delivery of vanadium and manganese chloride, both are insulin mimetics, have been shown to enhance bone fracture repair [52,53].

This present disclosure demonstrated the potential of $Na_2WO_4$ as an inductive agent for MSC chondrogenesis for cartilage tissue engineering applications. $Na_2WO_4$ may be used with MSC-based approaches to induce cartilage tissue formation. $Na_2WO_4$ could be combined with scaffolds to control the release of this compound or it could be delivered locally through direct injection to enhance chondrogenesis.

Piezo-Electric Composite Scaffold

The present disclosure also relates to a composite scaffold capable of supporting cell and tissue growth and bone growth. Depending on the implementation the piezo-electric composite may be used in combination with the above embodiments or alone such as previously described for the above embodiments. In particular, the present disclosure includes a composite scaffold that contains nanoparticles and a synthetic polymer or a naturally-derived polymer.

In one embodiment, zinc oxide (ZnO) was fabricated into a flexible 3-D fibrous scaffold by embedding zinc oxide nanoparticles into a slow degrading polycaprolactone (PCL) fiber using a biomimetic approach. While the use of ZnO, which has piezoelectric properties, is exemplary, it will be understood that other suitable piezoelectric materials, such as but not limited to, triglycine sulfate, sodium tungstate, and betaine-selenious acid, could be used. The scaffold could be biodegradable, biocompatible, or both.

The amount of zinc oxide nanoparticles could vary depending on the properties desired. In one embodiment, the amount of zinc oxide nanoparticles could be 1, 2, 5, or 10 wt % of PCL, depending on the implementation.

Although polycaprolactone was used, it will be understood that other synthetic polymers could be used. The synthetic polymer can be a single polymer or copolymer. Suitable polymers can include poly (α-hydroxy acids), such as the polyesters. The synthetic polymer can be selected from the group consisting of polylactic acid, poly L-lactic acid, polyglycolic acid, polylactic co-glycolic acid, polycaprolactone, poly methacrylate co-n-butyl methacrylate, poly dimethyl siloxane, polyethylene oxide and combinations thereof. It can also be naturally-derived polymers, such as collagen, gelatin, cellulose and its derivatives, and zein.

Zinc ions can be released from the fiber over time which may be beneficial for cell function since zinc has well known insulin mimetic properties. Insulin and insulin growth factors play important role in chondrogenesis and cartilage formation.

In one embodiment, ZnO-PCL composite fibrous scaffolds were evaluated for mesenchymal stem cells (MSCs) chondrogenesis, examining MSC growth and differentiation by matrix production. Depending on the embodiment, the scaffold could contain whole bone marrow or mesenchymal stem cells.

The below example is given to illustrate the principles stated. It should be understood that the example, which indicating one embodiment, is given by way of illustration only and is not meant to limit the scope of the invention. While this embodiment discusses the use of specific compounds and materials, it is understood that the method could be employed using similar materials. Similar quantities or measurements may be substituted without altering the method embodied below.

In one embodiment, 1, 2.5, 5, and 10 wt % of ZnO nanoparticles (100 nm) to PCL were dissolved in methylene chloride. Nonwoven fibrous ZnO-PCL composite scaffolds were fabricated using electrospinning. As is known in the art, electrospinning is used to fabricate tissue engineering scaffolds by applying a high voltage to a solution. The basic principle behind this process is that an electric voltage sufficient enough to overcome the surface tension of a solution causes the droplets to elongate so that the material is splayed randomly as very fine fibers, which when collected on a grounded metal plate, form a non-woven mat or mesh.

Scanning electron microscopy (SEM) and Image J software were used to determine the fiber morphology and the average fiber diameter. 10 mm samples were incubated in phosphate-buffered saline (PBS) and the release of zinc were determined by using inductive coupled plasma mass spectrometry (ICP-MS) over time.

Human MSCs were seeded onto the scaffolds at $1.76*10^5$ cells/cm$^2$ and cultured for 28 days in chondrogenic induction media. Samples were harvested and analyzed at days 14 and 28. Cell number (n=4 per group) was determined using PicoGreen® ds DNA assay (Invitrogen). Immunostaining for collagen type II and cell morphology using actin staining were evaluated by confocal microscopy.

Figure 12A:
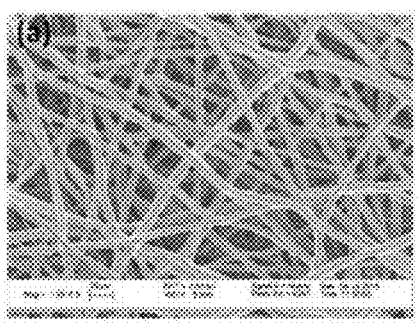
FIGS. 12a-c illustrates SEM images showing fiber morphology of (a) PCL, (b) 1% ZnO, and (c) 10% ZnO, where the scale bar=20 µm.
Figure 12B:
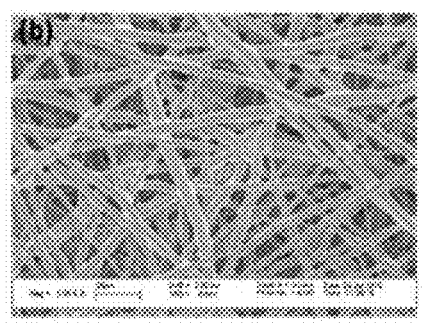
Figure 12C:
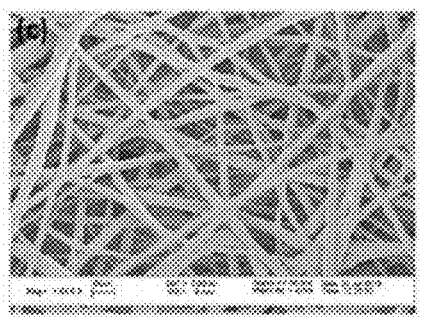
Figure 13:
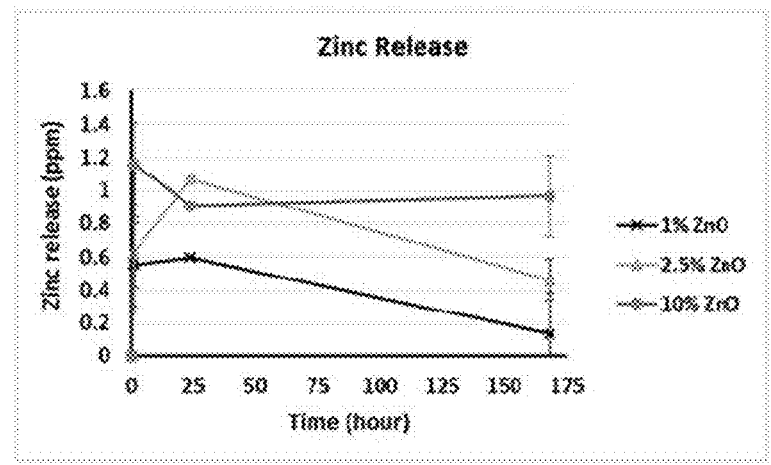
FIG. 13 is a chart showing zinc release from scaffolds with concentrations of 1%, 2.5%, and 10% of zinc oxide.
Figure 14:
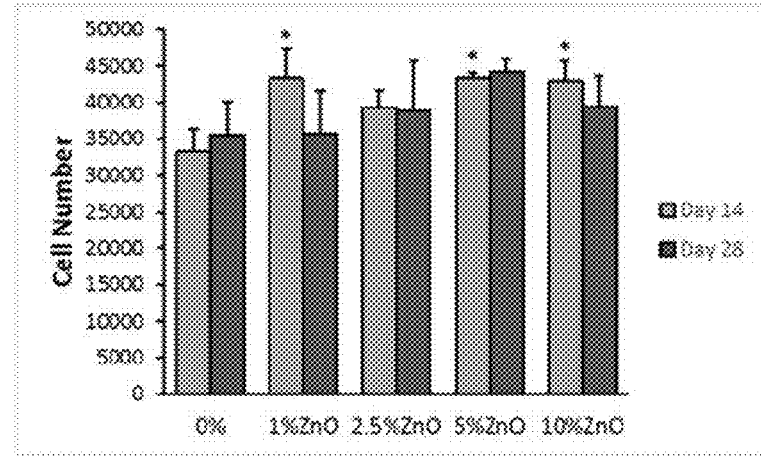
FIG. 14 is a chart showing cell number at days 14 and 28 on ZnO-PCL scaffolds, where *P<0.05.
Figures 15A, 15B, 15C, 15D:
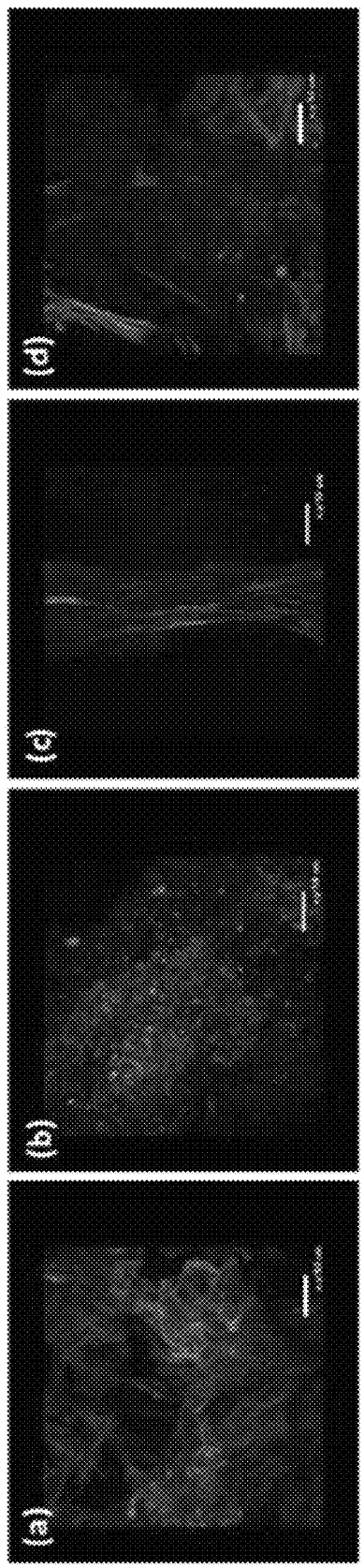
FIGS. 15a-d are confocal microscopic images showing collagen type II (red), Actin (green) and nucleus (blue) on (a) PCL control, (b) 1% ZnO (c) 5% ZnO and (d) 10% ZnO composite, where the scale bar=50 µm.

The results will now be described. With reference to FIGS. 12a-c, SEM images showed comparable fiber morphology, fiber diameters, and interfiber spacing in the micron-range of different ZnO composite scaffolds. As shown in FIG. 13, zinc release was higher for higher concentrations of ZnO in the composite scaffolds after days 1 and 7, which could contribute to MSCs chondrogenesis. Referring to FIG. 14, there was a significant increase in cell number in ZnO composite groups as compared with PCL alone at day 14. As shown in the confocal images of FIGS. 15a-d, cells also appeared to produce more collagen type II in ZnO composite groups as compared to control.

ZnO composite scaffolds support cell growth and attachment. ZnO composite can promote chondrogenic differentiation of MSCs as observed by an increase in collagen type 2 production. This disclosure demonstrated the feasibility of ZnO as a potential scaffold for cartilage tissue engineering.

Figure 16A:
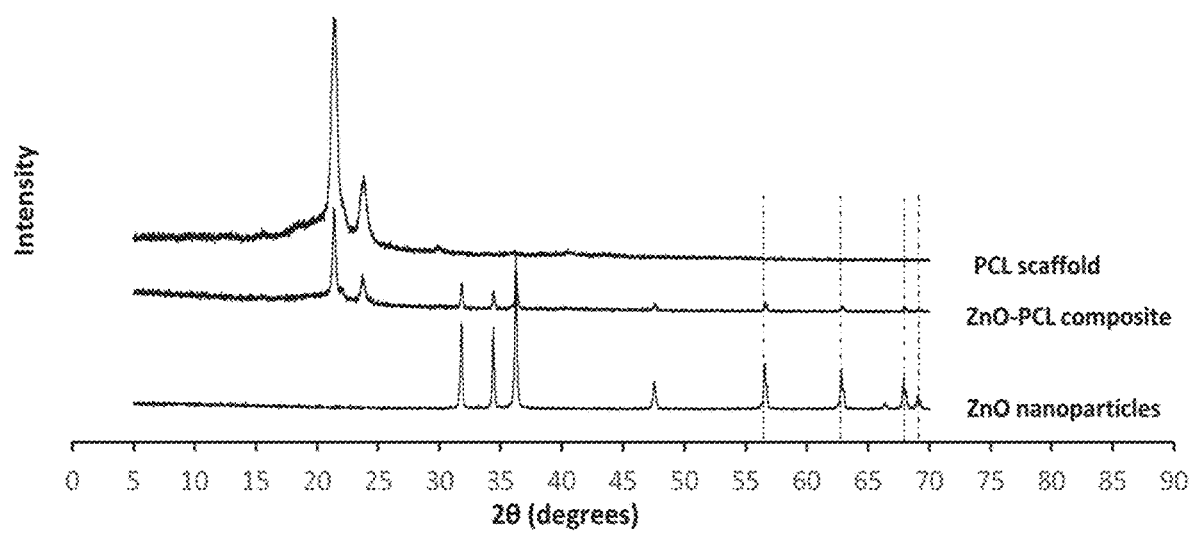
FIG. 16a illustrates XRD of PCL, ZnO composite scaffolds and ZnO nanoparticles.
Figure 16B:
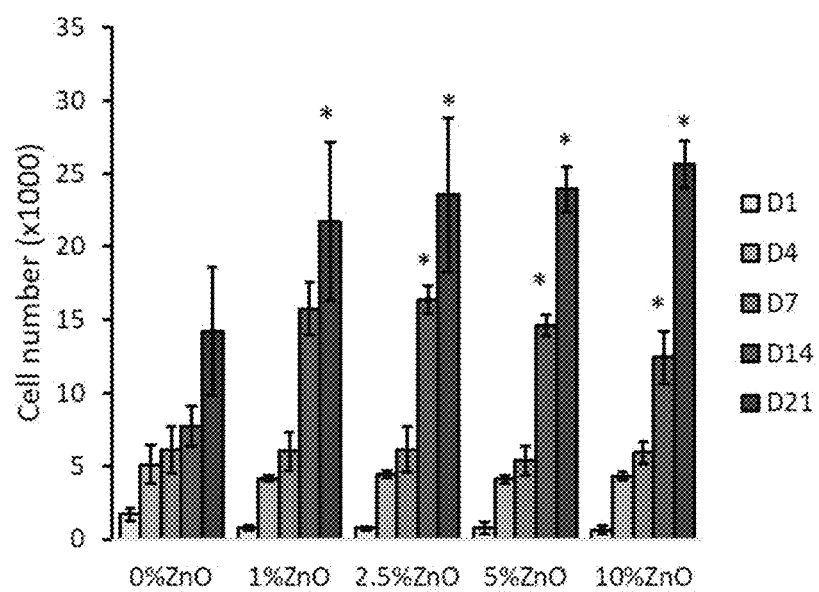
FIG. 16b illustrates cell number and (C) and alkaline phosphatase activity (ALP)
Figure 16C:
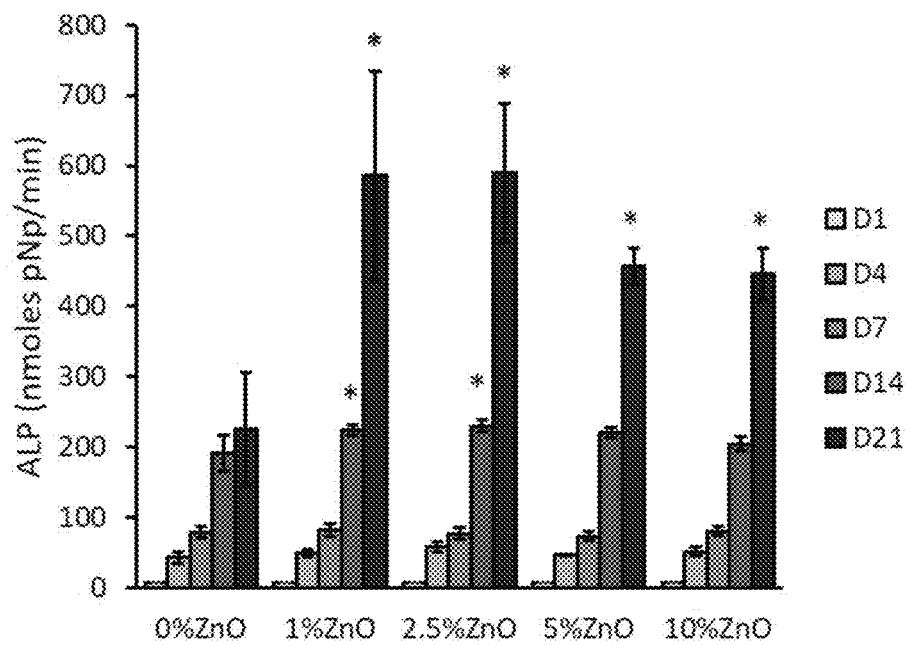
FIG. 16c illustrates collagen content on ZnO Composite scaffolds where *P<0.05 as compared to PCL alone (0%)

Adverting to FIGS. 16a-c and and 17a-b, shown are the following. Bone and cartilage tissue have known piezoelectric properties, which means they can generate electrical activity in response to mechanical deformation. Using a biomimetic approach, Zinc oxide (ZnO), which has known piezoelectric properties, was fabricated into a flexible 3-D fibrous scaffold by embedding ZnO nanoparticles into a slow degrading polycaprolactone (PCL) fiber. Zinc ions are released from the fiber over time which also may be beneficial for cell function since zinc has well known insulin mimetic properties. It has been shown that local insulin delivery to bone fracture site in diabetic and normal animal models improved healing and bone regeneration. As discussed above, ZnO-PCL composite fibrous scaffolds were evaluated for supporting mesenchymal stem cell (MSC) osteogenesis. The following is another example of such scaffolds.

Materials and Methods: 1, 2.5, 5 and 10 wt % of ZnO nanoparticles to PCL were dissolved in methylene chloride. Nonwoven fibrous ZnO-PCL composite scaffolds were fabricated using electrospinning Scanning electron microscopy (SEM) and Image J software were used to determine the fiber morphology and the average fiber diameter. X-Ray Diffraction (XRD) was used to determine piezoelectric crystal structure of ZnO. Human MSCs were seeded onto the scaffolds at $3.5 \times 10^4$ cells/cm and cultured for 21 days in osteogenic and growth media. Samples were harvested and analyzed for cell proliferation by using PicoGreen® ds DNA assay (Invitrogen) and alkaline phosphatase activity (ALP) based on the conversion of para-nitrophenyl phosphate (p-NPP) to para-nitrophenol (p-NP). Immunostaining for collagen type I and cell morphology using actin staining were evaluated by confocal microscopy. Hydroxyproline assay was used to measure total collagen.

Results and Discussion: SEM images showed comparable fiber morphology, fiber diameters and interfiber spacing in the micron-range of different ZnO composite scaffolds as shown in FIGS. 16a-c. ZnO-PCL composite has characteristic peaks for the piezoelectric ZnO crystal structure as shown in FIG. 16a. There was a significant increase in cell number in ZnO composite groups as compared with PCL alone at days 14 and 21 as seen in FIG. 16b.

Figure 17A:
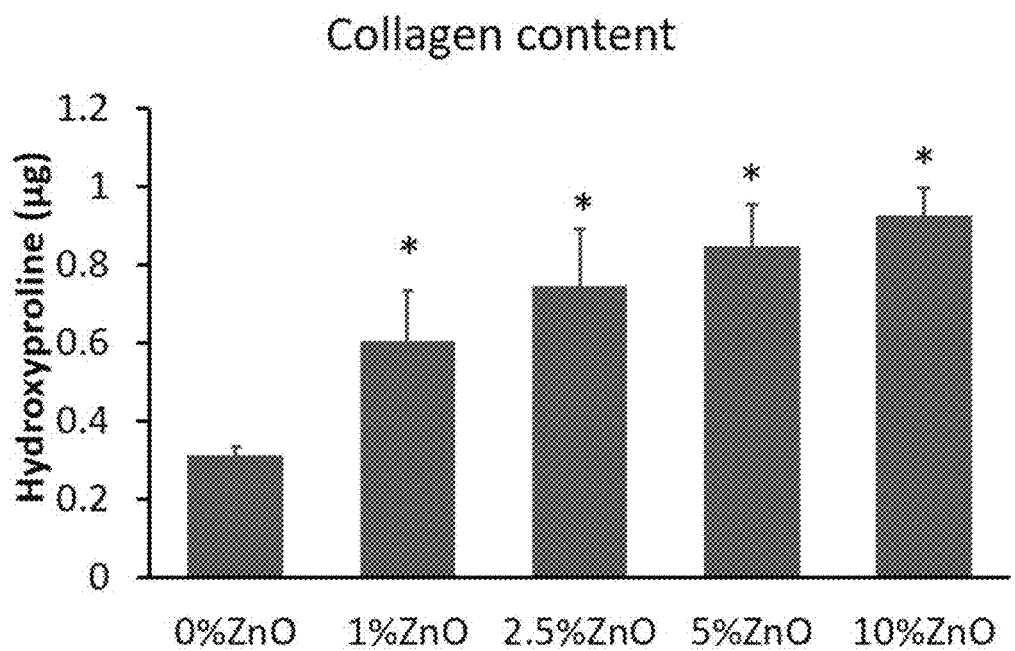
FIG. 17a is a bar chart showing collagen content on ZnO Composite scaffolds.

MSC osteogenesis was enhanced on ZnO composite scaffolds as compared with control as shown by ALP activity and total collagen production as shown in FIGS. 16c and 17a, respectively).

Figure 17B:
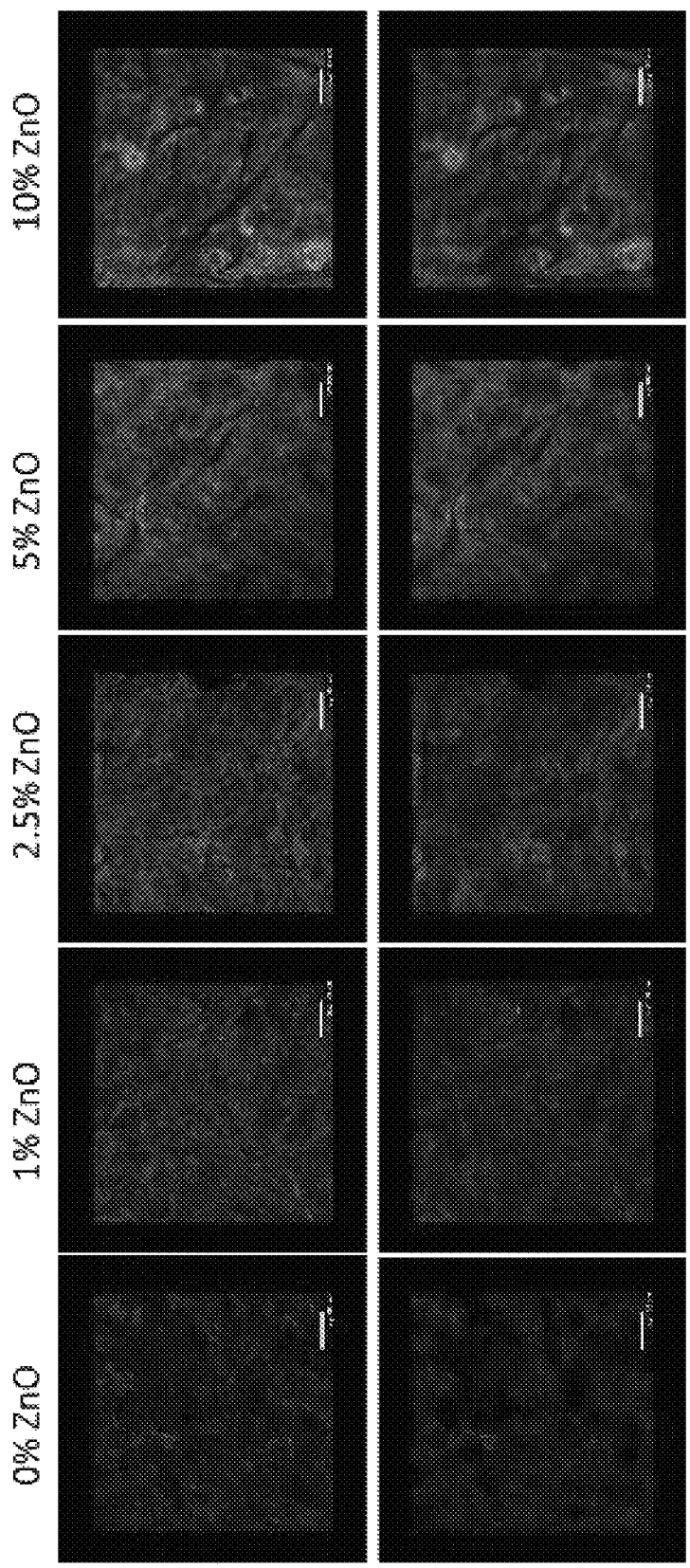
FIG. 17b are confocal images showing collagen type I (green), Actin (red) and nucleus (blue) on ZnO composite scaffolds where the scale bar=100 µm.

Cells also appeared to produce more collagen type I in ZnO composite groups as compared to control as shown in FIG. 17b. Electrospun ZnO composite scaffolds enhanced osteogenic differentiation of MSCs.

More specifically, FIG. 16a is a XRD of PCL, ZnO composite scaffolds and ZnO nanoparticles, FIG. 16b illustrates cell number and (C) and alkaline phosphatase activity (ALP) and FIG. 16c shows collagen content on ZnO Composite scaffolds .*P<0.05 as compared to PCL alone (0%).

FIG. 17a shows collagen content on ZnO Composite scaffolds and FIG. 17b shows confocal images illustrating collagen type I (green), Actin (red) and nucleus (blue) on ZnO composite scaffolds. The scale bar=100 μm.

The present disclosure found that ZnO composite scaffolds support cell growth and attachment. ZnO composite can promote osteogenic differentiation of MSCs as observed by an increase in ALP activity, collagen type 1 and osteocalcin production. Again, this disclosure demonstrated the feasibility of ZnO as a potential scaffolds for bone tissue engineering. Other applications may include loading to the scaffolds to investigate the effect of piezoelectric activity on the MSC osteogenesis.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

REFERENCES

1. Makris E A, A H Gomoll, K N Malizos, J C Hu and K A Athanasiou. (2015). Repair and tissue engineering techniques for articular cartilage. Nat Rev Rheumatol 11:21-34.
2. Madeira C, A Santhagunam, J B Salgueiro and J M Cabral. (2015). Advanced cell therapies for articular cartilage regeneration. Trends Biotechnol 33:35-42.
3. Abrams G, N Mall, L Fortier, B Roller and B Cole. (2013). BioCartilage: Background and Operative Technique. Operative Techniques in Sports Medicine 21:116-24.
4. Murphy L and C G Helmick. (2012). The impact of osteoarthritis in the United States: a population-health perspective: A population-based review of the fourth most common cause of hospitalization in U.S. adults. Orthop Nurs 31:85-91.
5. Roos H, T Adalberth, L Dahlberg and L Lohmander. (1995). Osteoarthritis of the Knee after Injury to the Anterior Cruciate Ligament or Meniscus: The Influence of Time and Age. Osteoarthritis and Cartilage 3:261-7.
6. Ullah I, R B Subbarao and G J Rho. (2015). Human mesenchymal stem cells—current trends and future prospective. Biosci Rep 35.
7. Vega A, M A Martin-Ferrero, F Del Canto, M Alberca, V Garcia, A Munar, L Orozco, R Soler, J J Fuertes, M Huguet, A Sanchez and J Garcia-Sancho. (2015). Treatment of Knee Osteoarthritis With Allogeneic Bone Marrow Mesenchymal Stem Cells: A Randomized Controlled Trial. Transplantation 99:1681-90.
8. Diekman B O, C R Rowland, D P Lennon, A I Caplan and F Guilak. (2010). Chondrogenesis of adult stem cells from adipose tissue and bone marrow: induction by growth factors and cartilage-derived matrix. Tissue Eng Part A 16:523-33.
9. Lin Z, C Willers, J Xu and M H Zheng. (2006). The chondrocyte: biology and clinical application. Tissue Eng 12:1971-84.
10. Longobardi L, L O'Rear, S Aakula, B Johnstone, K Shimer, A Chytil, W A Horton, H L Moses and A Spagnoli. (2006). Effect of IGF-I in the chondrogenesis of bone marrow mesenchymal stem cells in the presence or absence of TGF-beta signaling. J Bone Miner Res 21:626-36.
11. Kellner K, M B Schulz, A Gopferich and T Blunk. (2001). Insulin in tissue engineering of cartilage: a potential model system for growth factor application. J Drug Target 9:439-48.
12. Beam H A, J R Parsons and S S Lin. (2002). The effects of blood glucose control upon fracture healing in the BB Wistar rat with diabetes mellitus. J Orthop Res 20:1210-6.
13. Park A G, D N Paglia, L Al-Zube, J Hreha, S Vaidya, E Breitbart, J Benevenia, J P O'Connor and S S Lin. (2013). Local insulin therapy affects fracture healing in a rat model. J Orthop Res 31:776-82.
14. Dedania J, R Borzio, D Paglia, E A Breitbart, A Mitchell, S Vaidya, A Wey, S Mehta, J Benevenia, J P O'Connor and S S Lin. (2011). Role of local insulin augmentation upon allograft incorporation in a rat femoral defect model. J Orthop Res 29:92-9.
15. Brange J and L Langkjoer. (1993). Insulin structure and stability. Pharm Biotechnol 5:315-50.
16. Barbera A, J E Rodriguez-Gil and J J Guinovart. (1994). Insulin-like actions of tungstate in diabetic rats. Normalization of hepatic glucose metabolism. J Biol Chem 269:20047-53.
17. Nocito L, D Zafra, J Calbo, J Dominguez and J J Guinovart. (2012). Tungstate reduces the expression of gluconeogenic enzymes in STZ rats. PLoS One 7:e42305.
18. Munoz M C, A Barbera, J Dominguez, J Fernandez-Alvarez, R Gomis and J J Guinovart. (2001). Effects of tungstate, a new potential oral antidiabetic agent, in Zucker diabetic fatty rats. Diabetes 50:131-8.
19. Barbera A, J Fernandez-Alvarez, A Truc, R Gomis and J J Guinovart. (1997). Effects of tungstate in neonatally streptozotocin-induced diabetic rats: mechanism leading to normalization of glycaemia. Diabetologia 40:143-9.
20. Dominguez J E, M C Munoz, D Zafra, I Sanchez-Perez, S Baque, M Caron, C Mercurio, A Barbera, R Perona, R Gomis and J J Guinovart. (2003). The antidiabetic agent 21. Rodriguez-Gallardo J, R A Silvestre, E M Egido and J Marco. (2000). Effects of sodium tungstate on insulin and glucagon secretion in the perfused rat pancreas. Eur J Pharmacol 402:199-204.
22. Gomez-Ramos A, J Dominguez, D Zafra, H Corominola, R Gomis, J J Guinovart and J Avila. (2006). Sodium tungstate decreases the phosphorylation of tau through GSK3 inactivation. J Neurosci Res 83:264-73.
23. Gomez-Ramos A, J Dominguez, D Zafra, H Corominola, R Gomis, J J Guinovart and J Avila. (2006). Inhibition of GSK3 dependent tau phosphorylation by metals. Curr Alzheimer Res 3:123-7.
24. Arita N A, D Pelaez and H S Cheung. (2011). Activation of the extracellular signal-regulated kinases 1 and 2 (ERK1/2) is needed for the TGFbeta-induced chondrogenic and osteogenic differentiation of mesenchymal stem cells. Biochem Biophys Res Commun 405:564-9.
25. Chang Y, S W Ueng, S Lin-Chao and C C Chao. (2008). Involvement of Gas7 along the ERK1/2 MAP kinase and SOX9 pathway in chondrogenesis of human marrow-derived mesenchymal stem cells. Osteoarthritis Cartilage 16:1403-12.
26. Shanmugasundaram S, H Chaudhry and T L Arinzeh. (2011). Microscale versus nanoscale scaffold architecture for mesenchymal stem cell chondrogenesis. Tissue Eng Part A 17:831-40.
27. Selmi T A, P Verdonk, P Chambat, F Dubrana, J F Potel, L Barnouin and P Neyret. (2008). Autologous chondrocyte implantation in a novel alginate-agarose hydrogel: outcome at two years. J Bone Joint Surg Br 90:597-604.
28. Dhollander A A, P C Verdonk, S Lambrecht, R Verdonk, D Elewaut, G Verbruggen and K F Almqvist. (2012). Midterm results of the treatment of cartilage defects in the knee using alginate beads containing human mature allogenic chondrocytes. Am J Sports Med 40:75-82.
29. Patlolla A, G Collins and T L Arinzeh. (2010). Solvent-dependent properties of electrospun fibrous composites for bone tissue regeneration. Acta Biomater 6:90-101.
30. Desai M B, T Gavrilova, J Liu, S A Patel, S Kartan, S J Greco, E Capitle and P Rameshwar. (2013). Pollen-induced antigen presentation by mesenchymal stem cells and T cells from allergic rhinitis. Clin Transl Immunology 2:e7.
31. Jaiswal N, S E Haynesworth, A I Caplan and S P Bruder. (1997). Osteogenic differentiation of purified culture-expanded human mesenchymal stem cells in vitro. Journal of Cellular Biochemistry 64:295-312.
32. Dominici M, K Le Blanc, I Mueller, I Slaper-Cortenbach, F Marini, D Krause, R Deans, A Keating, D Prockop and E Horwitz. (2006). Minimal criteria for defining multipotent mesenchymal stromal cells. The International Society for Cellular Therapy position statement. Cytotherapy 8:315-7.
33. Pittenger M F, A M Mackay, S C Beck, R K Jaiswal, R Douglas, J D Mosca, M A Moorman, D W Simonetti, S Craig and D R Marshak. (1999). Multilineage potential of adult human mesenchymal stem cells. Science 284:143-7.
34. Haynesworth S, M Baber and A Caplan. (1992). Cell Surface Antigens on Human Marrow-Derived Mesenchymal Stem Cells are Detected by Monoclonal Antibodies. J Cell Physiol 138:8-16.
35. Kapoor S, S A Patel, S Kartan, D Axelrod, E Capitle and P Rameshwar. (2012). Tolerance-like mediated suppression by mesenchymal stem cells in patients with dust mite allergy-induced asthma. J Allergy Clin Immunol 129: 1094-101.
36. Greco S J, S A Patel, M Bryan, L F Pliner, D Banerjee and P Rameshwar. (2011). AMD3100-mediated production of interleukin-1 from mesenchymal stem cells is key to chemosensitivity of breast cancer cells. Am J Cancer Res 1:701-15.
37. Bertinat R, F Nualart, X Li, A J Yanez and R Gomis. (2015). Preclinical and Clinical Studies for Sodium Tungstate: Application in Humans. J Clin Cell Immunol 6.
38. Phornphutkul C, K Y Wu and P A Gruppuso. (2006). The role of insulin in chondrogenesis. Mol Cell Endocrinol 249:107-15.
39. Mueller M B, T Blunk, B Appel, A Maschke, A Goepferich, J Zellner, C Englert, L Prantl, R Kujat, M Nerlich and P Angele. (2013). Insulin is essential for in vitro chondrogenesis of mesenchymal progenitor cells and influences chondrogenesis in a dose-dependent manner Int Orthop 37:153-8.
40. Gandhi A, H A Beam, J P O'Connor, J R Parsons and S S Lin. (2005). The effects of local insulin delivery on diabetic fracture healing. Bone 37:482-90.
41. Zafra D, L Nocito, J Dominguez and J J Guinovart. (2013). Sodium tungstate activates glycogen synthesis through a non-canonical mechanism involving G-proteins. FEBS Lett 587:291-6.
42. Rizza R A, L J Mandarino and J E Gerich. (1981). Dose-reponse characteristics for effects of insulin on production and utilization of glucose in man American Journal of Physiology 240:E630-E639.
43. Guandalini G S, L Zhang, E Fornero, J A Centeno, V P Mokashi, P A Ortiz, M D Stockelman, A R Osterburg and G G Chapman. (2011). Tissue distribution of tungsten in mice following oral exposure to sodium tungstate. Chem Res Toxicol 24:488-93.
44. Kelly A D, M Lemaire, Y K Young, J H Eustache, C Guilbert, M F Molina and K K Mann. (2013). In vivo tungsten exposure alters B-cell development and increases DNA damage in murine bone marrow. Toxicol Sci 131:434-46.
45. Nagareddy P R, H Vasudevan and J H McNeill. (2005). Oral administration of sodium tungstate improves cardiac performance in streptozotocin-induced diabetic rats. Can J Physiol Pharmacol 83:405-11.
46. Hanzu F, R Gomis, M J Coves, J Viaplana, M Palomo, A Andreu, J Szpunar and J Vidal. (2010). Proof-of-concept trial on the efficacy of sodium tungstate in human obesity. Diabetes Obes Metab 12:1013-8.
47. Osterburg A R, C T Robinson, S Schwemberger, V Mokashi, M Stockelman and G F Babcock. (2010). Sodium tungstate (Na2WO4) exposure increases apoptosis in human peripheral blood lymphocytes. J Immunotoxicol 7:174-82.
48. Mourino V, J P Cattalini and A R Boccaccini. (2012). Metallic ions as therapeutic agents in tissue engineering scaffolds: an overview of their biological applications and strategies for new developments. J R Soc Interface 9:401-19.
49. Taylor A. (1985). Therapeutic uses of trace elements. Clin Endocrinol Metab 14:703-24.
50. Li N and Y Zheng. (2013). Novel Magnesium Alloys Developed for Biomedical Application: A Review. Journal of Materials Science & Technology 29:489-502.
51. Lee J W, H S Han, K J Han, J Park, H Jeon, M R Ok, H K Seok, J P Ahn, K E Lee, D H Lee, S J Yang, S Y Cho, P R Cha, H Kwon, T H Nam, J H Han, H J Rho, K S Lee, Y C Kim and D Mantovani. (2016). Long-term clinical study and multiscale analysis of in vivo biodegradation mechanism of Mg alloy. Proc Natl Acad Sci USA 113: 716-21.

52. Paglia D N, A Wey, A G Park, E A Breitbart, S K Mehta, J D Bogden, F W Kemp, J Benevenia, J P O'Connor and S S Lin. (2012). The effects of local vanadium treatment on angiogenesis and chondrogenesis during fracture healing. J Orthop Res 30:1971-8.

53. Hreha J, A Wey, C Cunningham, E S Krell, E A Brietbart, D N Paglia, N J Montemurro, D A Nguyen, Y J Lee, D Komlos, E Lim, J Benevenia, J P O'Connor and S S Lin. (2015). Local manganese chloride treatment accelerates fracture healing in a rat model. J Orthop Res 33:122-30.

What is claimed is:

1. An insulin-mimetic for cartilage, bone, or osteochondral repair, comprising:
   (a) 0.01-0.1 mM sodium tungstate ($Na_2WO_4$); and
   (b) a composite scaffold including a polymer and 1-10% zinc oxide (ZnO) embedded in the scaffold,
   Wherein cells can propagate on the scaffold, and
   Wherein the sodium tungstate is as an inductive agent and its concentration of 0.01-0.1 mM enhances human mesenchymal stem cell (MSC) chondrogenesis, as compared to an anti-diabetic concentration of 6 mM.

2. The insulin-mimetic of claim 1, wherein the sodium tungstate (Na2WO4) is at a concentration of 0.01 mM.

3. The insulin-mimetic of claim 1, wherein the cells acquire an organization and produce cartilage, bone or both cartilage and bone.

4. The insulin-mimetic of claim 3, wherein the composite scaffold is a piezo-electric composite scaffold that does not utilize an external power source.

5. The insulin-mimetic of claim 1, wherein the polymer is naturally or synthetically derived.

6. The insulin-mimetic of claim 5, wherein the polymer is selected from the group consisting of polycaprolactone (PCL), poly ($\alpha$-hydroxy acids), polyesters, a polylactic acid, poly L-lactic acid, polyglycolic acid, polylactic co-glycolic acid, poly methacrylate co-n-butyl methacrylate, poly dimethyl siloxane, polyethylene oxide, collagen, gelatin, cellulose and its derivatives, zein, and any combinations thereof.

7. The insulin-mimetic of claim 1, wherein cytocompatibility in a presence of the concentration of sodium tungstate ($Na_2WO_4$) between 0.01 mM to 0.1 mM Na2WO4 is comparable to an absence of Na2WO4.

8. An insulin-mimetic for cartilage, bone, or osteochondral repair, comprising:
   0.01-0.1 mM sodium tungstate ($Na_2WO_4$); and
   a piezo-electric composite scaffold including a polymer and 1-10% zinc oxide,
   wherein the sodium tungstate is an inductive agent that enhances human mesenchymal stem cell (MSC) chondrogenesis at the concentration of 0.01-0.1 mM.

9. The insulin-mimetic of claim 8, wherein the polymer is a slow degrading polycaprolactone (PCL) fiber, and the zinc oxide is zinc oxide nanoparticles embedded in the fiber.

10. The insulin-mimetic of claim 9, wherein the scaffold further includes whole bone marrow or mesenchymal stem cells.

* * * * *